(12) United States Patent
Goldstein et al.

(10) Patent No.: US 11,065,593 B2
(45) Date of Patent: *Jul. 20, 2021

(54) MICROCAPSULES ENCAPSULATING A REFLECTIVE AGENT

(71) Applicant: Tagra Biotechnologies Ltd., Natania (IL)

(72) Inventors: Danny Goldstein, Kibbutz Dafna (IL); Shaher Duchi, Kfar Rama (IL); Lior Ben-Altabet, Kibbutz Dafna (IL); Yaniv Menachem, Moshav Dishon (IL); Olga Privalova, Kibbutz LeHavot HaBashan (IL); Hanan Haj, Rehaniya (IL); Audrey Ricard, La varenne Saint Hilaire (FR)

(73) Assignee: Tagra Biotechnologies Ltd., Natania (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/756,621

(22) PCT Filed: Sep. 2, 2016

(86) PCT No.: PCT/IL2016/050964
§ 371 (c)(1),
(2) Date: Mar. 1, 2018

(87) PCT Pub. No.: WO2017/037716
PCT Pub. Date: Mar. 9, 2017

(65) Prior Publication Data
US 2018/0243718 A1    Aug. 30, 2018

Related U.S. Application Data

(60) Provisional application No. 62/213,690, filed on Sep. 3, 2015.

(51) Int. Cl.
*B01J 13/12*  (2006.01)
*A61K 8/20*  (2006.01)
(Continued)

(52) U.S. Cl.
CPC .................. *B01J 13/12* (2013.01); *A61K 8/11* (2013.01); *A61K 8/19* (2013.01); *A61K 8/20* (2013.01);
(Continued)

(58) Field of Classification Search
None
See application file for complete search history.

(56) References Cited

U.S. PATENT DOCUMENTS

| 4,756,906 A | 7/1988 | Sweeny |
| 5,320,835 A | 6/1994 | Pahlck et al. |

(Continued)

FOREIGN PATENT DOCUMENTS

| AR | 047879 | 3/2006 |
| AR | 056580 | 10/2007 |

(Continued)

OTHER PUBLICATIONS

International Preliminary Report on Patentability dated Mar. 15, 2018 From the International Bureau of WIPO Re. Application No. PCT/IL2016/050964. (7 Pages).

(Continued)

*Primary Examiner* — Kyung S Chang

(57) ABSTRACT

Microcapsules encapsulating a reflective agent are provided herein. The microcapsules are comprised of an inner core, which comprises the reflective agent and optionally an oily substance, and an outer shell formed of wall-forming polymeric materials. The microcapsules may further comprise an opaque substance and/or a fatty acyl salt in the outer shell. Processes of preparing the microcapsules are also provided.

5 Claims, 4 Drawing Sheets

(51) Int. Cl.
  *A61K 8/36* (2006.01)
  *A61K 8/73* (2006.01)
  *A61K 8/81* (2006.01)
  *A61K 9/48* (2006.01)
  *A61K 9/50* (2006.01)
  *A61K 8/29* (2006.01)
  *A61K 8/11* (2006.01)
  *A61Q 1/02* (2006.01)
  *A61K 8/19* (2006.01)
  *A61K 8/37* (2006.01)

(52) U.S. Cl.
  CPC ............... *A61K 8/29* (2013.01); *A61K 8/361* (2013.01); *A61K 8/37* (2013.01); *A61K 8/731* (2013.01); *A61K 8/8147* (2013.01); *A61K 8/8152* (2013.01); *A61K 9/485* (2013.01); *A61K 9/4858* (2013.01); *A61K 9/5026* (2013.01); *A61K 9/5042* (2013.01); *A61Q 1/02* (2013.01); *A61K 2800/42* (2013.01); *A61K 2800/651* (2013.01); *A61K 2800/652* (2013.01)

(56) References Cited

U.S. PATENT DOCUMENTS

| | | |
|---|---|---|
| 5,380,485 A | 1/1995 | Takahashi et al. |
| 5,382,433 A | 1/1995 | Pahlck et al. |
| 6,087,003 A | 7/2000 | Benoit et al. |
| 6,906,015 B1 | 6/2005 | Shiloach et al. |
| 6,932,984 B1 | 8/2005 | Babtsov et al. |
| 7,622,132 B2 | 11/2009 | Lee et al. |
| 7,648,715 B2 | 1/2010 | Mistry et al. |
| 7,671,005 B2 | 3/2010 | Mort, III et al. |
| 7,838,037 B2 | 11/2010 | Kvitnitsky et al. |
| 7,964,178 B2 | 6/2011 | Gutkowski et al. |
| 8,679,629 B2 | 3/2014 | Zhao et al. |
| 2004/0120908 A1 | 6/2004 | Cohen et al. |
| 2004/0136933 A1 | 7/2004 | Mistry et al. |
| 2005/0031558 A1 | 2/2005 | Elder et al. |
| 2005/0048014 A1 | 3/2005 | Linz et al. |
| 2005/0181969 A1 | 8/2005 | Mort, III et al. |
| 2005/0276774 A1 | 12/2005 | Elder et al. |
| 2006/0252667 A1 | 11/2006 | Mort, III et al. |
| 2006/0292193 A1 | 12/2006 | Lee et al. |
| 2007/0020208 A1 | 1/2007 | Gutkowski et al. |
| 2007/0071978 A1 | 3/2007 | Sojka et al. |
| 2007/0196502 A1 | 8/2007 | Mort, II et al. |
| 2007/0249512 A1 | 10/2007 | Mort et al. |
| 2007/0249513 A1 | 10/2007 | Mort et al. |
| 2009/0155371 A1 | 6/2009 | Sojka et al. |
| 2010/0095868 A1 | 4/2010 | Kaupp et al. |
| 2010/0113321 A1 | 5/2010 | Mort, III et al. |
| 2010/0267604 A1 | 10/2010 | Mort, III et al. |
| 2010/0291014 A1 | 11/2010 | Tellefsen et al. |
| 2010/0297045 A1 | 11/2010 | Kaupp et al. |
| 2011/0003152 A1 | 1/2011 | Grey |
| 2011/0067735 A1 | 3/2011 | Mort, III et al. |
| 2011/0118384 A1 | 5/2011 | Bugnon et al. |
| 2011/0124545 A1 | 5/2011 | Mort, III et al. |
| 2011/0159060 A1 | 6/2011 | Khan et al. |
| 2011/0165208 A1 | 7/2011 | Kim et al. |
| 2011/0223224 A1 | 9/2011 | Mathonnet et al. |
| 2011/0268778 A1 | 11/2011 | Dihora et al. |
| 2011/0268802 A1 | 11/2011 | Dihora et al. |
| 2011/0269657 A1 | 11/2011 | Dihora et al. |
| 2011/0269658 A1 | 11/2011 | Dihora et al. |
| 2012/0076843 A1 | 3/2012 | Jung et al. |
| 2012/0269752 A1 | 10/2012 | Ozee et al. |
| 2012/0276031 A1 | 11/2012 | Wei et al. |
| 2014/0037703 A1 | 2/2014 | Dihora et al. |
| 2014/0227328 A1 | 8/2014 | Dihora et al. |
| 2014/0335138 A1* | 11/2014 | Goldstein ............... B01J 13/12 424/401 |
| 2015/0132791 A1 | 5/2015 | Nagai |

FOREIGN PATENT DOCUMENTS

| | | |
|---|---|---|
| AT | 176764 | 3/1999 |
| AT | 309305 | 11/2005 |
| AU | 2002316861 | 11/2002 |
| AU | 2006261991 | 1/2007 |
| AU | 2006294882 | 4/2007 |
| AU | 2006213970 | 11/2007 |
| BR | 0603808 | 3/2009 |
| CA | 2201864 | 3/2004 |
| CA | 2505963 | 6/2004 |
| CA | 2612226 | 1/2007 |
| CA | 2645504 | 1/2007 |
| CA | 2622465 | 4/2007 |
| CA | 2559145 | 10/2007 |
| CA | 2645501 | 11/2007 |
| CA | 2647429 | 12/2007 |
| CA | 2669239 | 7/2008 |
| CA | 2444715 | 7/2009 |
| CA | 2795616 | 7/2010 |
| CA | 2795617 | 7/2010 |
| CA | 2795618 | 7/2010 |
| CA | 2800456 | 7/2010 |
| CA | 2776338 | 7/2011 |
| CN | 1507476 | 6/2004 |
| CN | 1244642 | 3/2006 |
| CN | 101041746 | 9/2007 |
| CN | 101309746 | 11/2008 |
| CN | 101402903 | 4/2009 |
| CN | 101426895 | 5/2009 |
| CN | 101426896 | 5/2009 |
| CN | 101443438 | 5/2009 |
| CN | 101541416 | 9/2009 |
| CN | 101891969 | 11/2010 |
| CN | 101965383 | 2/2011 |
| CN | 102015914 | 4/2011 |
| CN | 102458641 | 5/2012 |
| CN | 102638988 | 8/2012 |
| CN | 102858940 | 1/2013 |
| CN | 102858944 | 1/2013 |
| CN | 102883803 | 1/2013 |
| CN | 102892492 | 1/2013 |
| CN | 103589530 | 2/2014 |
| CN | 103622842 | 3/2014 |
| CN | 103764271 | 4/2014 |
| CN | 103911023 | 7/2014 |
| CN | 104039393 | 9/2014 |
| CN | 104161684 | 11/2014 |
| CN | 104168870 | 11/2014 |
| CN | 104168959 | 11/2014 |
| CN | 104812359 | 7/2015 |
| DE | 69507891 | 10/1999 |
| DE | 60207237 | 7/2006 |
| DK | 0784506 | 9/1999 |
| EP | 0706821 | 4/1996 |
| EP | 0784506 | 2/1999 |
| EP | 2687590 | 1/2001 |
| EP | 1518903 | 3/2005 |
| EP | 1387867 | 11/2005 |
| EP | 1881059 | 1/2008 |
| EP | 2093260 | 8/2009 |
| EP | 2250995 | 11/2010 |
| EP | 1567111 | 8/2011 |
| EP | 2371907 | 10/2011 |
| EP | 2687287 | 1/2014 |
| ES | 2130666 | 7/1999 |
| ES | 2369051 | 11/2011 |
| ES | 2372384 | 1/2012 |
| FR | 2841155 | 12/2003 |
| FR | 2935265 | 3/2010 |
| GR | 3030282 | 9/1999 |
| IN | 225025 | 11/2005 |
| JP | 10-510243 | 10/1998 |
| JP | 2004-531609 | 10/2004 |
| JP | 2006-508982 | 3/2006 |
| JP | 2007-291318 | 11/2007 |
| JP | 4141845 | 8/2008 |
| JP | 2009-509967 | 3/2009 |
| JP | 2009-532576 | 9/2009 |

(56) References Cited

FOREIGN PATENT DOCUMENTS

| | | |
|---|---|---|
| JP | 2009-532577 | 9/2009 |
| JP | 2009-533205 | 9/2009 |
| JP | 2008-543946 | 12/2009 |
| JP | 2009-298792 | 12/2009 |
| JP | 2010-510337 | 4/2010 |
| JP | 2010-510877 | 4/2010 |
| JP | 2010-270330 | 12/2010 |
| JP | 2010-270337 | 12/2010 |
| JP | 2011-079804 | 4/2011 |
| JP | 2011-515508 | 5/2011 |
| JP | 2011-520000 | 7/2011 |
| JP | 2011-529104 | 12/2011 |
| JP | 2012-529981 | 11/2012 |
| JP | 5078227 | 11/2012 |
| JP | 2013516411 | 5/2013 |
| JP | 2013-525564 | 6/2013 |
| JP | 2013-525565 | 6/2013 |
| JP | 2013-531694 | 8/2013 |
| JP | 2014-037549 | 2/2014 |
| JP | 2014-051670 | 3/2014 |
| JP | 2014-159584 | 9/2014 |
| KR | 2003-097849 | 1/2003 |
| KR | 10-0858835 | 12/2003 |
| KR | 2007-104195 | 10/2007 |
| KR | 10797738 | 1/2008 |
| KR | 20080019022 | 2/2008 |
| KR | 2008-0034214 | 4/2008 |
| KR | 20090079957 | 7/2009 |
| KR | 100978583 | 8/2010 |
| KR | 2010-0118151 | 11/2010 |
| KR | 2010126744 | 12/2010 |
| KR | 10-1075327 | 10/2011 |
| KR | 2012-0046166 | 5/2012 |
| KR | 2012091579 | 8/2012 |
| KR | 2013-0000417 | 1/2013 |
| MS | 2008013449 | 10/2008 |
| MX | 2003010086 | 3/2004 |
| MX | 06010625 | 10/2007 |
| MX | 2008013356 | 10/2008 |
| MX | 2008013357 | 10/2008 |
| MX | 2009005006 | 5/2009 |
| MX | 2012004435 | 5/2012 |
| MX | 2012012549 | 11/2012 |
| MX | 2012012550 | 11/2012 |
| MX | 2012012551 | 11/2012 |
| NO | 20034853 | 10/2003 |
| NO | 325737 | 7/2008 |
| RU | 2003133772 | 5/2005 |
| RU | 2008138395 | 5/2010 |
| RU | 2012142724 | 6/2014 |
| RU | 2012142728 | 6/2014 |
| RU | 2012144736 | 6/2014 |
| TW | 201141535 | 12/2011 |
| WO | WO 96/11055 | 4/1996 |
| WO | WO 98/05002 | 2/1998 |
| WO | WO 02/090445 | 11/2002 |
| WO | WO 2004/041234 | 5/2004 |
| WO | WO 2004/045524 | 6/2004 |
| WO | WO 2004/075679 | 9/2004 |
| WO | WO 2005/080542 | 9/2005 |
| WO | WO 2007/002431 | 1/2007 |
| WO | WO 2007/011432 | 1/2007 |
| WO | WO 2007/038404 | 4/2007 |
| WO | WO 2007/124370 | 11/2007 |
| WO | WO 2007/124371 | 11/2007 |
| WO | WO 2007/146491 | 12/2007 |
| WO | WO2008/058868 | 5/2008 |
| WO | WO 2009/079135 | 6/2009 |
| WO | WO 2009/103322 | 8/2009 |
| WO | WO 2009/135784 | 11/2009 |
| WO | WO 2009/138978 | 11/2009 |
| WO | WO 2010/026312 | 3/2010 |
| WO | WO 2010/079466 | 7/2010 |
| WO | WO 2010/079467 | 7/2010 |
| WO | WO 2010/079468 | 7/2010 |
| WO | WO 2010/084480 | 7/2010 |
| WO | WO 2010/145993 | 12/2010 |
| WO | WO 2011/027960 | 3/2011 |
| WO | WO 2011/042902 | 4/2011 |
| WO | WO 2011/082019 | 7/2011 |
| WO | WO 2011/082032 | 7/2011 |
| WO | WO 2013/107353 | 7/2013 |
| WO | WO 2014/082299 | 6/2014 |
| WO | WO 2014/132261 | 9/2014 |
| WO | WO 2015/132791 | 9/2015 |
| WO | WO 2015/132792 | 9/2015 |
| WO | WO 2015/166448 | 11/2015 |
| WO | WO-2015166454 A1 * 11/2015 ............. A61K 8/345 |
| WO | WO 2017/037716 | 3/2017 |
| ZA | 200808683 | 11/2009 |
| ZA | 200808684 | 11/2009 |
| ZA | 200808862 | 1/2010 |

OTHER PUBLICATIONS

International Search Report and the Written Opinion dated Mar. 1, 2017 From the International Searching Authority Re. Application No. PCT/IL2016/050964. (11 Pages).
Communication Pursuant to Article 94(3) EPC dated Sep. 6, 2019 From the European Patent Office Re. Application No. 16795437.9. (6 Pages).
Communication Pursuant to Article 94(3) EPC dated Sep. 25, 2020 From the European Patent Office Re. Application No. 16795437.9. (5 Pages).
Notice of Reasons for Rejection dated Jun. 23, 2020 From the Japan Patent Office Re. Application No. 2018-511153 and Its Translation Into English. (17 Pages).
Notification of Office Action and Search Report dated Jun. 16, 2020 From the State Intellectual Property Office of the People's Republic of China Re. Application No. 201680057254.4. (10 Pages).
Translation Dated Jul. 19, 2020 of Notification of Office Action dated Jun. 16, 2020 From the State Intellectual Property Office of the People's Republic of China Re. Application No. 201680057254.4. (7 Pages).
Office Action dated Mar. 23, 2020 From the Israel Patent Office Re. Application No. 257821 and Its Translation Into English. (6 Pages).
Translation Dated Mar. 30, 2021 of Notification of Office Action dated Mar. 10, 2021 From the State Intellectual Property Office of the People's Republic of China Re. Application No. 201680057254.4. (8 Pages).
Notice of Reason(s) for Rejection dated Mar. 2, 2021 From the Japan Patent Office Re. Application No. 2018-511153 and Its Translation Into English. (5 Pages).
Notification of Office Action dated Mar. 10, 2021 From the State Intellectual Property Office of the People's Republic of China Re. Application No. 201680057254.4. (8 Pages).
Office Action Dated May 18, 2021 From the Israel Patent Office Re. Application No. 257821 and Its Translation Into English. (7 Pages).

* cited by examiner

MICROCAPSULES ENCAPSULATING A REFLECTIVE AGENT

NAMES AND PARTIES TO A JOINT RESEARCH AGREEMENT

The invention disclosed and claimed herein was made by or on behalf of parties to a joint research agreement directed to preparation of various capsules for cosmetic applications that was in effect on or before the date the claimed invention was made. The names of the parties to the joint research agreement are Tagra Biotechnologies Ltd. and L'Oreal.

RELATED APPLICATIONS

This application is a National Phase of PCT Patent Application No. PCT/IL2016/050964 having International filing date of Sep. 2, 2016, which claims the benefit of priority under 35 USC § 119(e) of U.S. Provisional Patent Application No. 62/213,690 filed on Sep. 3, 2015. The contents of the above applications are all incorporated by reference as if fully set forth herein in their entirety.

FIELD AND BACKGROUND OF THE INVENTION

The present invention, in some embodiments thereof, relates to encapsulation and, more particularly, but not exclusively, to microcapsules encapsulating a reflective agent, and to processes of preparing same.

In cosmetic formulations it is highly desirable to retain a cosmetically active agent, including pigment, dyes, colorants and other agents that provide a visual effect within capsules before application thereof. Encapsulation of such agents is thought for in order to maintain a long term visual effect of the cosmetic formulation; to protect the encapsulated agent from interacting with other agents in the formulation; to mask the visual effect of the active agent before application; to maintain the stability of the active agent in a formulation and/or to release the encapsulated active agent only upon application. The effectiveness of protection/masking by single-layer microencapsulation depends on the chemical structure, molecular weight and physical properties of the microencapsulated ingredient.

Microparticles encapsulating a variety of cosmetically active agents, including colorants and/or pigments and other agents that provide a visual effect, have been described in the art.

U.S. Pat. Nos. 5,320,835 and 5,382,433 disclose "activatable" dormant colored particles or pigments and cosmetic formulations comprising them and further comprising a colored base phase, and colorant entrapping substrate particles dispersed in said base phase. The encapsulated colorants are said to be released into the base phase when mechanical action is applied to the cosmetic formulation, and produce an intense shade in the color of the base phase, whereas the colorant entrapping substrate particles entrap the released colorants and produce a subtle shade in the color of the base phase. The encapsulated pigments are made by a coacervation method.

WO 98/5002 discloses similar color-sustainable base cosmetic formulations, further including volatile solvents to minimize the gritty feel of the microencapsulated material. The color obtained from the released encapsulated pigments is exactly the same as the color of the composition itself. Releasing provides renewed intensity of the original base color.

U.S. Pat. No. 5,380,485 discloses colored cosmetic compositions, comprising particulate fillers coated with polymer that is combined with colorants, and their application in decorative cosmetics.

U.S. Patent Application having Publication Nos. 2005/0031558 and 2005/0276774 disclose a personal care or cosmetic composition containing microparticles comprising a shatter resistant blend of distinct colorants microencapsulated within a polymer matrix, preferably a cross-linked polymer matrix that does not allow any of the entrapped colorant to be released even under prolonged use. The matrix polymer is preferably transparent or translucent such that the blend of encapsulated colorants provides the coloring of the cosmetic product itself and of the skin upon application of the cosmetic composition. The microparticles disclosed in U.S. Patent Application having Publication No. 2005/0276774 further contain secondary particles (i.e. hydrophobic polymers different from those of the matrix polymer) that are distributed throughout the matrix.

U.S. Pat. No. 4,756,906 discloses decorative cosmetic compositions containing a first colorant and microcapsules containing a solvated second colorant, different from the first colorant. Upon rupture of the microcapsules, the coloration of the encapsulated pigment is added into the composition thereby altering its color characteristics.

WO 2004/075679 discloses rigid, non-rupturable microcapsules containing a blend of at least two coloring agents and compositions comprising them, which do not change their color upon application onto the skin. The microcapsules are non-rupturable due to the use of cross-linked polymeric matrix comprising polymers that have a glass transition temperature (Tg) higher than 80° C.

U.S. Pat. No. 6,932,984, by the present assignee, discloses single- and double-layer microcapsules and a method for microencapsulation of substances by the solvent removal method using non-chlorinated solvents. The method is based on physical processes which do not cause any change of original physical and/or chemical properties, biological activity, and safety of raw materials during the process.

U.S. Pat. No. 7,838,037, by the present assignee, discloses double-layer and/or triple-layer microcapsules, designed to rupture by a slight mechanical action such as rubbing or pressing on the skin, and thereby immediately release their encapsulated content. These microcapsules are prepared by the solvent removal method using non-chlorinated solvents. This method affords physical stability to the microcapsules, high ability to entrap the active agents, protection of the active agents inside the microcapsules, and prevention of the diffusion of the microencapsulated active agents to the external water phase in a water-based preparation.

WO 2009/138978, by the present assignee, discloses cosmetic compositions for dermal/topical application comprising double-layer, rupturable microcapsules which contain one or more microencapsulated colorants. When applied to the skin, such compositions produce an immediate color change effect indicating the delivery to the skin of the active substances contained in said compositions.

Bismuth oxychloride is an inorganic compound of the formula BiOCl. Bismuth oxychloride, in powder or agglomerate form, has been used in foundations mostly as filler, intended to impart soft feel.

Bismuth oxychloride, due to its layered structure, imparts a pearly iridescent light reflectivity, and has also been used in cosmetic products for imparting a satiny, localized and discontinuous effect, which, in products such as fluids, compacts and powders, is perceived as a nacreous sheen.

WO 2004/041234 describes lightening and whitening anhydrous compositions comprising a Phyllanthus emblica (PE) extract and, as additive, bismuth oxychloride in the form of a powder or a dispersion, intended to give the composition a dry and soft feel on the skin.

Dispersions of bismuth oxychloride in 2-ethylhexyl hydroxystearate are marketed by Merck as Biron® Liquid Silver and Timiron® Liquid Silver. These dispersions are observed as a highly silvery and extremely shiny liquid, and are recommended by the supplier for uses in compositions of the gloss, varnish and eye shadow type. According to the supplier, it is a silvery-white paste which imparts a second dimension of pearlesense to cosmetic products.

U.S. Pat. No. 6,906,015 describes rinse-off cleansing compositions containing a dispersion of bismuth oxychloride.

U.S. Patent Application having Publication No. 2012/0269752 describes a use of bismuth oxychloride pre-dispersed in 2-ethylhexyl hydroxystearate in care and/or make-up products of emulsion type, which impart luminosity to the skin upon application.

While the use of bismuth oxychloride or a dispersion thereof in an oily substance has been recognized as beneficial in cosmetic application, it is limited by the disadvantages associated with the inclusion of bismuth oxychloride is cosmetic products.

The use of a bismuth oxychloride in a powder form or agglomerate is limited by its tendency to become white and thus affect the visual appearance of a product containing same upon application; by its effect on sensory properties such as freshness. Further, in order to achieve a sparkle effect, grinding of the powder into finer particles is required and thus poses an industrial constraint.

While using a dispersion of bismuth oxychloride dispersion in a polar oil overcomes some of these limitations, such a dispersion imparts to a product containing same a greasy feeling and high pearly shine, which are often undesirable, and thereby the amount of such a dispersion in a final product should be limited.

U.S. Patent Application having Publication No. 2010/095868, U.S. Pat. No. 7,622,132, PCT International Patent Application Publication No. WO 09/079135, and EP Patent No. 1518903B1, describe using a reflective agent such as nacre pigments containing bismuth oxychloride or bismuth oxychloride in microcapsules. Additional background art includes International Patent Application No. PCT/IL2015/050236.

SUMMARY OF THE INVENTION

The present invention, in some embodiments thereof, relates to microcapsules suitable for use in topical compositions and, more particularly, but not exclusively, to microcapsules comprising a reflective agent (e.g., in a form of a reflective particle) and to topical formulations comprising same, which can be used, for example, as or in cosmetic formulations and products.

According to an aspect of some embodiments of the present invention there is provided a microcapsule comprising an inner core enveloped by an outer shell formed of a wall-forming polymeric material, the inner core comprising a reflective agent.

According to some of any of the embodiments described herein, the outer shell further comprises an opaque substance.

According to some of any of the embodiments described herein, the opaque substance is selected from the group consisting of $TiO_2$, zinc oxide, alumina, boron nitride, talc, kaolin, mica and any combination thereof.

According to some of any of the embodiments described herein, the opaque substance comprises $TiO_2$.

According to some of any of the embodiments described herein, an amount of the opaque substance ranges from about 1% to about 60%, or from about 5% to about 50%, or from about 10% to about 40%, by weight of the total weight of the microcapsule.

According to some of any of the embodiments described herein, the microcapsule further comprises a fatty acid salt.

According to some of any of the embodiments described herein, the fatty acid is selected from the group consisting of stearic acid, arachidic acid, palmitoleic acid, oleic acid, linoleic acid, linolaidic acid, arachidonic acid, myristoleic acid and erucic acid.

According to some of any of the embodiments described herein, the fatty acid salt is selected from the group consisting of magnesium stearate, magnesium oleate, calcium stearate, calcium linoleate, and sodium stearate.

According to some of any of the embodiments described herein, the fatty acid salt comprises magnesium stearate.

According to some of any of the embodiments described herein, an amount of the fatty acid salt ranges from about 0.05% to about 5%, or from about 0.1% to about 3%, or from about 0.5% to about 2.0%, or from about 0.5% to about 1.5%, by weight, of the total weight of the microcapsule.

According to some of any of the embodiments described herein, the wall-forming polymeric material comprises a polymer or copolymer selected from the group consisting of a polyacrylate, a polymethacrylate, a cellulose ether, a cellulose ester, copolymers thereof and any combination thereof.

According to some of any of the embodiments described herein, the polymer or copolymer is selected from the group consisting of a polyacrylate, a polymethacrylate, an acrylate/ammonium methacrylate copolymer, an ammonium methacrylate copolymer type B, low molecular weight (about 15,000 Dalton) poly(methyl methacrylate)-co-(methacrylic acid), poly(ethyl acrylate)-co-(methyl methacrylate)-co-(trimethyl ammonium-ethyl methacrylate chloride), poly (butyl methacrylate)-co-(2-dimethy laminoethyl methacrylate)-co-(methyl methacrylate)), poly(styrene)-co-(maleic anhydride), copolymer of octylacrylamide, cellulose ether, cellulose ester, poly(ethylene glycol)-block-poly(propylene glycol)-block-poly(ethylene glycol), PLA (poly lactic acid), PGA (poly glycolic acid) and PLGA copolymer.

According to some of any of the embodiments described herein, the wall-forming material comprises a polymer or copolymer selected from the group consisting of poly(m-ethyl methacrylate), poly(methyl methacrylate)-co-(methacrylic acid), cellulose acetate, and an acrylate/ammonium methacrylate copolymer.

According to some of any of the embodiments described herein, the wall-forming material comprises poly(methyl methacrylate).

According to some of any of the embodiments described herein, an amount of the wall-forming polymeric material ranges from about 1% to about 50%, or from about 1% to about 20%, or from about 5% to about 10%, by weight, of the total weight of the microcapsule.

According to some of any of the embodiments described herein, the reflective agent is selected from the group consisting of bismuth oxychloride, a mica coated by titanium dioxide, particles featuring a metallic glint and a mixture thereof.

According to some of any of the embodiments described herein, the reflective agent is in a form of particles.

According to some of any of the embodiments described herein, the inner core further comprises an oily substance.

According to some of any of the embodiments described herein, the inner core comprises particles of the reflective agent dispersed in, or mixed with, an oily substance.

According to some of any of the embodiments described herein, the oily substance is selected from the group consisting of a plant oil, a mineral oil, a triglyceride, a fatty ester, and a fatty alcohol.

According to some of any of the embodiments described herein, the oily substance is selected from almond oil, wheat germ oil, jojoba oil, apricot oil, soya bean oil, canola oil, castor oil, octyl dodecanol, octyldodecyl neopentanoate, a caprylic/capric triglyceride, pentaerythrityl tetraisostearate, isodecyl neopentanoate, diisopropyl sebacate, $C_{12}$-$C_{15}$ alkyl benzoate, ethylhexyl ethylhexanoate, 2-ethylhexyl hydroxystearate, and any mixture thereof.

According to some of any of the embodiments described herein, the oily substance is selected from castor oil and 2-ethylhexyl hydroxystearate.

According to some of any of the embodiments described herein, the inner core comprises particles of the reflective agent dispersed in, or mixed with, an oily substance selected from castor oil, 2-ethylhexyl hydroxystearate and a mixture thereof.

According to some of any of the embodiments described herein, the inner core comprises bismuth oxychloride and 2-ethylhexyl hydroxystearate.

According to some of any of the embodiments described herein, an amount of the inner core is at least 50 weight percents of the total weight of the microcapsule.

According to some of any of the embodiments described herein, an amount of the inner core ranges from about 50% to about 90%, by weight, of the total weight of the microcapsule.

According to some of any of the embodiments described herein, an amount of the inner core ranges from about 60% to about 90%, or from about 60% to about 80%, or from about 70% to about 80%, by weight, of the total weight of the microcapsule.

According to some of any of the embodiments described herein, the microcapsule further comprises a plasticizer.

According to some of any of the embodiments described herein, the plasticizer is selected from the group consisting of triethyl citrate, tricaprylin, trilaurin, tripalmitin, triacetin, acetyltriethyl citrate, paraffin oil, and any combination thereof.

According to some of any of the embodiments described herein, the plasticizer is triethyl citrate.

According to some of any of the embodiments described herein, an amount of the plasticizer ranges from about 0.5% to about 20%, or from about 1% to about 20%, or from about 5% to about 15%, by weight, of the total weight of the microcapsule.

According to some of any of the embodiments described herein, the outer shell comprises:

the wall-forming polymeric material in an amount that ranges from about 5% to about 15%, by weight, of the total weight of the microcapsule;

the opaque substance in an amount that ranges from about 0 to about 30%, by weight, of the total weight of the microcapsule; and the fatty acid salt in an amount that ranges from about 0 to about 2%, by weight, of the total weight of the microcapsule.

According to some of any of the embodiments described herein, the wall-forming polymeric material is selected from selected from the group consisting of poly(methyl methacrylate), poly(methyl methacrylate)-co-(methacrylic acid), cellulose acetate, and an acrylate/ammonium methacrylate copolymer;

the opaque substance is titanium dioxide;

the fatty acid salt is magnesium stearate; and the inner core comprises particles of bismuth oxychloride dispersed in 2-ethylhexyl hydroxystearate.

According to some of any of the embodiments described herein, the microcapsule is a single-layer microcapsule.

According to an aspect of some embodiments of the present invention there is provided a composition comprising a plurality of microcapsules, at least a portion of the microcapsules comprising a plurality of the microcapsules as described herein in any of the respective embodiments. The composition is a non-cosmetic composition.

According to an aspect of some embodiments of the present invention there is provided a plurality of microcapsules, at least a portion of the microcapsules comprising the microcapsules as described herein in any of the respective embodiments.

According to some of any of the embodiments described herein, at least 50%, or at least 80%, or at least 90% of the microcapsules are the microcapsules described herein.

According to some of any of the embodiments described herein, substantially all of the microcapsules are the microcapsules as described herein.

According to some of any of the embodiments described herein, a mean size of the plurality of microcapsules ranges from about 100 μm to about 200 μm.

According to an aspect of some embodiments of the present invention there is provided a process of preparing the composition as described herein in any of the respective embodiments or the plurality of microcapsules as described herein in any of the respective embodiments, the process comprising:

(a) contacting a first organic phase comprising the reflective agent, a wall-forming polymer or copolymer, optionally a fatty acid salt, and optionally an opaque substance, and a partially water-miscible organic solvent with an aqueous continuous phase saturated with the organic solvent and comprising an emulsifier, and optionally an opaque substance, to thereby obtain an emulsion; and (b) adding to the formed emulsion an amount of water which initiates extraction of the organic solvent from the emulsion, thereby obtaining the microcapsules.

According to some of any of the embodiments described herein, the process further comprises isolating the microcapsules.

According to some of any of the embodiments described herein, the process further comprises drying and sifting the microcapsules, to thereby obtain a free flowing powder of the microcapsules.

According to some of any of the embodiments described herein, the organic solvent is selected from ethyl acetate, ethanol, ethyl formate, and any combination thereof.

According to some of any of the embodiments described herein, the plurality of microcapsules as described herein is prepared by the process as described herein in any one of the respective embodiments.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
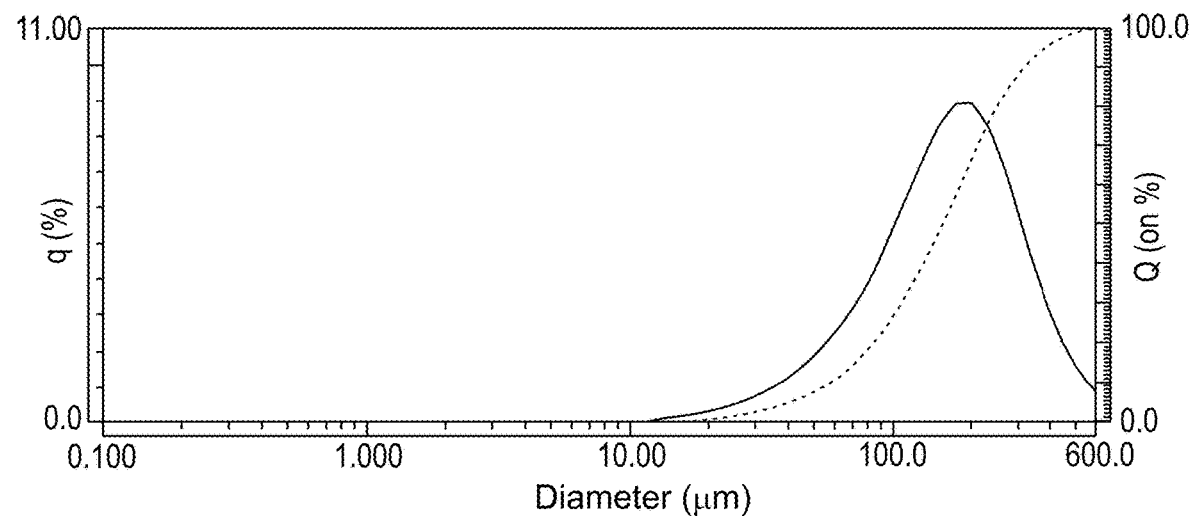
FIGS. 1, 2, 3 and 4 present data obtained for the size distribution of a plurality of microcapsules obtained as described in Example 1 (FIG. 1), Example 2 (FIG. 2), Example 3 (FIG. 3) and Example 5 (FIG. 4), respectively, according to exemplary embodiments of the present invention.

The present invention, in some embodiments thereof, relates to encapsulation and, more particularly, but not exclusively, to microcapsules encapsulating a reflective agent, and to processes of preparing same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, bismuth oxychloride is known to provide nacre-like, or pearly, effect, and has been used in various cosmetic formulations, mostly in its solid form. As further discussed hereinabove, when provided as dispersion in an oily vehicle, bismuth oxychloride provides a continuous luminous effect upon application to the skin. However, as further discussed hereinabove, the inclusion of bismuth oxychloride or an oily dispersion containing same in cosmetic formulations often adversely affects the formulations and/or fails to achieve the desired effect of bismuth oxychloride.

The present inventors have designed and successfully practiced a novel methodology for efficiently encapsulating, in core-shell microcapsules, a reflective agent such as bismuth oxychloride, and particularly a reflective agent which, as a raw material, is pre-dispersed in an oily vehicle, for example, bismuth oxychloride pre-dispersed in 2-ethylhexyl hydroxystearate. The present inventors have shown that using this novel methodology, encapsulation of the reflective agent in high load (e.g., higher than 50%, 60% and even higher than 70%, of the total weight of the microcapsule) is enabled. The microcapsules obtained by this methodology, while encapsulating the reflective agent in high load, and even when the reflective agent is encapsulated in a form of a dispersion, are provided as a free-flowing powder, are stable during the manufacturing and storage processes, are stable within cosmetic formulations, maintain the encapsulated agent inside the capsules with minimal or nullified leakage, and are rupturable under mild shear forces, thus enabling an immediate release of the encapsulated agent upon application of the microcapsules to the skin. The obtained microcapsules provided herewith may further provide a masking effect of the light reflectance of the reflective agent before rupture, if desired.

Some embodiments of the present invention relate to single-layer, core-shell microcapsules, encapsulating a reflective agent, as described herein, which, on one hand, exhibit exceptional, unexpected, stability when compounded in industrial processes and when maintained in various formulations, including aqueous formulations and various emulsion-type formulations, may exhibit masking of the reflective agent encapsulated therein, and provide an adequate protection from "bleeding" effect within various cosmetic formulations and, on the other hand, are readily rupturable only by applying a mechanical pressure/shear force such as rubbing action of a formulation containing same onto skin, thereby releasing the encapsulated agent. Multi-layer microcapsules encapsulating a reflective agent, as described herein, are also contemplated.

The methodology utilized for preparing the microcapsules is based on physical processes which do not cause any change to the original physical and/or chemical properties and safety of raw materials during the process. This method affords physical stability of the microcapsules, ability to entrap the reflective agent in high load, protection of the reflective agent inside the microcapsules, and prevention of the diffusion of the encapsulated agent to the external medium in both oil-based, water-based, and emulsion-type preparations (before application).

Thus, the present inventors have designed and successfully practiced a novel methodology for obtaining stable microcapsules, effectively concealing the light reflectance effect of the encapsulated agent contained therein, and exhibiting smooth and pleasant spread of the microcapsules upon application and immediate release of the encapsulated reflective agent by mere rubbing the formulations on the skin.

For example, the present inventors have demonstrated that microcapsules encapsulating a pre-dispersion of bismuth oxychloride in an oily vehicle exhibit increase in lightness values ($\Delta L^*$) compared to the raw material, remain stable under low shear forces commonly used in manufacturing cosmetic formulations, and remain stable when mixed with various cosmetic formulations, without being ruptured, and without affecting the formulation (e.g., without phase separation of an emulsion formulation).

Embodiments of the present invention therefore relate to a microcapsule comprising an inner core enveloped by an outer shell. The outer shell is formed of a wall-forming polymeric material, and the inner core comprises a reflective agent.

Embodiments of the present invention further relate to a composition comprising a plurality of microcapsules, at least a portion of the microcapsules comprising an inner core enveloped by an outer shell, wherein the inner core comprises a reflective agent, as described herein.

In some embodiments, when a dispersion of the reflective agent (e.g., bismuth oxychloride) is used as a raw material and is encapsulated, the obtained microcapsules may be regarded as a solid form of the pasty dispersion, which thus facilitate the utilization of this agent during manufacturing and storage of a cosmetic formulation that contains this agent.

The Microcapsules:

The microcapsules provided by the present embodiments are particles (e.g., generally spherical particles), which are generally closed structures containing an encapsulated (enveloped, entrapped) reflective agent, optionally in combination with an oily substance. The microcapsules generally have a core-shell structural feature, namely each microcapsule is comprised of a polymeric shell and a core that comprises the reflective agent or may be consisted of the reflective agent, with or without an oily vehicle (as described herein), enveloped by the shell.

The shell of the microcapsule is typically applied as a wall-forming material and serves as a membrane for the encapsulated substance. In some embodiments, the outer shell exhibits some opacity, or otherwise a masking effect of the reflective agent, by virtue of inclusion of an opaque substance in the shell, optionally in combination with a fatty acid salt.

The outer shell may further comprise a plasticizer to control its hardness, and is designed such that the microcapsules are rupturable upon rubbing or pressing on the skin.

In some embodiments, the microcapsules are rupturable upon application of a mechanical pressure. In some embodiments, application of a mechanical pressure comprises a rubbing action (e.g., application of one or more circular motion(s) to microcapsules that contact a surface such as a skin tissue). In some embodiments, at least 20%, or at least 30%, or preferably at least 40% or at least 50%, or at least 60%, or at least 70% or at least 80%, or at least 90% or more, including 100%, of the microcapsules rupture upon being subjected to rubbing, for example, by circle motions (e.g., one or more, or two or more, circle motions).

In some of any of the embodiments described herein, the microcapsules are single-layer microcapsules, comprising a single outer shell enveloping the inner core.

In some other embodiments, the microcapsules are double-layer, or triple-layer, or multi-layer microcapsules, comprising additional one or more layers enveloping the shell that envelopes the inner core.

A multi-layer microcapsule is featured as comprising an inner core microcapsule comprising a core which comprises a reflective agent, as described herein, being enveloped by a first shell comprised of a first wall-forming material, and at least one additional shell comprised of a second wall forming material enveloping said first shell, which can be regarded as enveloping a single-layer microcapsule as described herein (comprising the reflective agent-containing inner core and a first shell of a first wall-forming material).

Each shell in the multi-layered microcapsules is typically and independently applied as a wall-forming material (e.g., a first, second, third and so forth wall-forming materials forming the first, second, third, and so forth, outer shells, respectively), and serves as a membrane for the encapsulated substance. In some embodiments, one or more, or each, of the outer shells in the multi-layered microcapsules according to these embodiments is optionally opaque by virtue of an opaque substance comprised therein, and/or further contains a fatty acid salt, as described herein.

The microcapsules of the present embodiments, among other uses, are suitable for inclusion in topical, e.g., cosmetic, cosmeceutical and pharmaceutical (e.g., dermatological), applications. When applied to the skin, the microcapsules are capable of being ruptured upon application of shear forces such as rubbing and pressing on the skin, but they remain intact in the formulation itself before application, and exhibit exceptional stability in water-based, oil-based, silicon-based and emulsion-type formulations. The microcapsules are hard enough to avoid destruction of the shells and realization of the content during production processes such as isolation/filtration, drying, sieving, etc., and/or during storage.

The microcapsules according to the present embodiments are also referred to herein as reflective agent-encapsulating microcapsules or as microcapsules encapsulating a reflective agent.

In some embodiments, the microcapsules encapsulating the reflective agent as described herein are prepared by a solvent removal method, as described hereinunder and exemplified in the Examples section that follows.

In some embodiments, a mean size of the microcapsules as described herein is within a range of from about 10 µm to about 400 µm, or from about 50 µm to about 350 µm, or from about 50 µm to about 250 µm, or from about 90 µm to about 250 µm, or from about 100 µm to about 200 µm, including any intermediate value or subranges therebetween.

By "size" it is meant a size of at least one cross-section of the microcapsules, preferably a diameter of the microcapsules.

Herein throughout, a "mean" diameter means an average size of the microcapsules. The size of the microcapsules may be measured by a Laser distribution size method and particularly by measuring the values D[50] and D[90].

D50 means the size of which 50% of the microcapsules do not exceed (and 50% of the microcapsules do exceed), and D90 means the size of which 90% of the microcapsules do not exceed (and 10% of the microcapsules do exceed).

In some of any of the embodiments described herein, the outer shell comprises, in addition to the wall-forming material, a fatty acid salt, and an opaque substance, as described herein.

According to some of any of the embodiments of the present invention, the microcapsules described herein exhibit masking of the luminous effect of the reflective agent, as reflected by a positive shift (delta) of the lightness value (L*) determined in X-rite measurements.

According to some of any of the embodiments of the invention, a microcapsule as described herein is rupturable or breakable when applied to the skin; that is, a microcapsule as described herein remains intact in a formulation containing same and during industrial processes, but readily breaks when pressed of rubbed on the skin. The non-breakability of the microcapsules before topical application thereof is routinely assessed by monitoring (e.g., using a light microscope) the ability of the microcapsules in a basic cream or lotion to sustain their size and shape when subjected to low shear mixing at e.g., 40-600 (or 80-100) rpm for 5-10 minutes at room temperature and at 40° C. A change of less than 10% in the microcapsule size is indicative of the non-breakability of the microcapsules upon routine industrial processes.

The microcapsules provided herein have shown exceptional stability in various formulation types, including water-in-oil and oil-in-water types of emulsion, and in aqueous gel formulations, as demonstrated in the Examples section that follows.

The Inner Core:

The inner core in the microcapsules described herein comprises a reflective agent.

As used herein, a "reflective agent" describes an agent which increases the diffuse light reflection of a substrate onto which it is applied. A reflective agent as described herein is typically intended to increase the light reflection of keratinous substrates, particularly the skin, and more particularly facial skin.

According to some embodiments of the invention, a reflective agent may comprise, or be in a form of, particles, whereby the particles are characterized by dimensions and arrangement (e.g., a layered structure), and other physical and chemical features, which, when applied to a surface, cause reflection of incident light with a sufficient intensity that is visible to the naked eye. As a result, a reflective agent provides the substrate onto which it is applied points of brightness that contrast with their surroundings by appearing to shine.

In some embodiments, the reflective agent provides for a continuous diffuse reflection over the skin, and imparts a light effect or luminosity to facial skin when applied thereon.

By "light" or "light effect" it is meant herein the reflection characteristic of light, diffuse reflection and continues on the skin. Since the skin naturally reflects part of the incident light, a "light effect" according to some embodiments of the invention can increase this reflection.

A "light reflection" or "light effect" or "luminosity" or "luminous effect" as described herein, can be determined as described in the Examples section that follows.

An exemplary reflective agent is bismuth oxychloride.

Other exemplary reflective agents include, but are not limited to, inorganic nacres, particles with metallic glint, micas and other inorganic pigments, and combination thereof.

Inorganic pigments that are usable in the context of these embodiments of the present invention include, but are not limited to, titanium oxides, zirconium oxides, cerium oxides, zinc oxides, iron oxides, chromium oxides, ferric blue, manganese violet, ultramarine blue and chromium hydrate.

Additional pigments that are usable in the context of these embodiments of the present invention include, but are not limited to, pigment structures of the sericite/brown iron oxide/titanium dioxide/silica type, or of $BaSO_4/TiO_2/FeSO_3$ type, of silica/iron oxide type, or silica microspheres containing iron oxide.

The term "nacres" describes iridescent or non-iridescent colored particles, either of a natural origin (e.g., produced by certain molluscs in their shell) or synthesized, which exhibit a color effect by featuring optical interference. The term "nacres" is also referred to herein as "nacreous pigments".

Exemplary nacreous pigments include, but are not limited to, titanium mica coated with an iron oxide, titanium mica coated with bismuth oxychloride, titanium mica coated with chromium oxide, titanium mica coated with an organic dye and also nacreous pigments based on bismuth oxychloride. These may also be mica particles at the surface of which are superposed at least two successive layers of metal oxides and/or of organic colorants.

Additional exemplary nacres include, but are not limited to, natural mica coated with titanium oxide, with iron oxide, with natural pigment or with bismuth oxychloride.

Commercially available nacres include, for example, the Timica, Flamenco and Duochrome (mica-based) nacres sold by the company BASF, the Timiron nacres sold by the company Merck, the Prestige mica-based nacres sold by the company Eckart, the following nacres based on natural mica: Sunpearl from the company Sun Chemical, KTZ from the company Kobo and Sunprizma from the company Sun Chemical, the Sunshine and Sunprizma nacres based on synthetic mica sold by the company Sun Chemical, and the Timiron Synwhite nacres based on synthetic mica sold by the company MERCK.

More particular examples include gold-colored nacres sold especially by the company BASF under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company BASF under the name Super bronze (Cloisonne); the orange nacres sold especially by the company BASF under the names Orange 363C (Cloisonne) and Orange MCR 101 (Cosmica) and by the company Merck under the names Passion orange (Colorona) and Matte orange (17449) (Microna); the brown-tinted nacres sold especially by the company BASF under the names Nuantique copper 340XB (Cloisonne) and Brown CL4509 (Chromalite); the nacres with a copper tint sold especially by the company BASF under the name Copper 340A (Timica); the nacres with a red tint sold especially by the company Merck under the name Sienna fine (17386) (Colorona); the nacres with a yellow tint sold especially by the company BASF under the name Yellow (4502) (Chromalite); the red-tinted nacres with a golden tint sold especially by the company BASF under the name Sunstone G012 (Gemtone); the pink nacres sold especially by the company BASF under the name Tan opale G005 (Gemtone); the black nacres with a golden tint sold especially by the company BASF under the name Nu antique bronze 240 AB (Timica); the blue nacres sold especially by the company Merck under the name Matte blue (17433) (Microna); the white nacres with a silvery tint sold especially by the company Merck under the name Xirona Silver; and the golden-green pinkish-orange nacres sold especially by the company Merck under the name Indian summer (Xirona), and mixtures thereof.

Exemplary particles with a metallic glint which are usable in the context of the present embodiments include, but are not limited to, particles of at least one metal and/or of at least one metal derivative, particles comprising a single-material or multi-material organic or inorganic substrate, at least partially coated with at least one layer with a metallic glint comprising at least one metal and/or at least one metal oxide, metal halide or metal sulfide, and mixtures of said particles.

Exemplary metals that may be present in such particles include, but are not limited to, Ag, Au, Cu, Al, Ni, Sn, Mg, Cr, Mo, Ti, Zr, Pt, Va, Rb, W, Zn, Ge, Te and Se, and mixtures or alloys thereof, preferably Ag, Au, Cu, Al, Zn, Ni, Mo and Cr and mixtures or alloys thereof.

Exemplary particles with metallic glint include, but are not limited to, aluminum particles, such as those sold under the names Starbrite 1200 EAC® by the company Siberline and Metalure® by the company Eckart; particles made of metal powders of copper or of alloy mixtures such as the references 2844 sold by the company Radium Bronze, metallic pigments, for instance aluminium or bronze, such as those sold under the names Rotosafe 700 from the company Eckart, silica-coated aluminium particles sold under the name Visionaire Bright Silver from the company Eckart, and metal alloy particles, for instance the silica-coated bronze (alloy of copper and zinc) powders sold under the name Visionaire Bright Natural Gold from the company Eckart.

Other particles are those comprising a glass substrate such as those sold by the company Nippon Sheet Glass under the names Microglass Metashine, Xirona from the company Merck, Ronastar from the company Merck, Reflecks from the company BASF and Mirage from the company BASF.

Additional exemplary reflective agents include, goniochromatic coloring agents such as, for example, multilayer interference structures and liquid-crystal coloring agents.

Other reflective agents would be readily recognized by those skilled in the art.

A reflective substance as described herein may be in a form of particles.

In some embodiments, the particles of a reflective substance can constitute the inner core per se. In these embodiments, the raw material to be encapsulated is, for example, a powder.

In some embodiments the size of the particles of the reflective agent is in a range of from about 1 micron to about 30 microns, or from about 5 microns to about 25 microns.

In some embodiments, the particles of a reflective substance are provided as a dispersion, namely, the raw material to be encapsulated is a dispersion of the particles in a vehicle (or carrier or dispersant). The raw material is referred to herein in such cases as a reflective agent pre-dispersed in the vehicle.

Herein throughout, a "raw material" refers to an encapsulated substance before is has been encapsulated to form an inner core of the microcapsule, namely the substance added to the encapsulation process as one of the starting materials.

In these embodiments, the inner core comprises a dispersion of the particles of the reflective agent and the vehicle, or a mixture of the particles and the vehicle.

In some embodiments, the vehicle is an oily substance, such that the raw material is made of particles of the reflective agent pre-dispersed in the oily substance and the inner core comprises particles of the reflective agent and the oily substance.

The term "oily substance" describes a water-immiscible non-aqueous substance which is liquid at room temperature (25° C.) and atmospheric pressure (760 mmHg), and encompasses, for example, fatty acids, fatty esters, fatty alcohols, plant oils, mineral oils, and certain types of triglycerides. In some embodiments, the oily substance is polar oil.

The term "polar oil", as used herein, refers to any oil having, at 25° C., a solubility parameter $\delta_d$ characteristic of dispersive interactions of greater than 16 and a solubility parameter $\delta_p$ characteristic of polar interactions strictly greater than 0. The solubility parameters $\delta_d$ and $\delta_p$ are defined according to the Hansen classification. For example, these polar oils may be chosen from esters, triglycerides and ethers.

The definition and calculation of the solubility parameters in the Hansen three-dimensional solubility space are described in the paper by C. M. Hansen: "The three dimensional solubility parameters", J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a=(\delta_p^2+\delta_h^2)^{1/2}$.

The parameters $\delta_p$, $\delta_h$, $\delta_D$ and $\delta_a$ are expressed in $(J/cm^3)^{1/2}$.

In some embodiments, the polar oil is an oil having $\delta_a$ greater than 6.

The polar oil may be of plant, mineral or synthetic origin.

In some embodiments, the polar oil is a non-volatile polar hydrocarbon-based oil.

The phrase "polar hydrocarbon-based oil" means a polar oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The term "non-volatile oil" means an oil that remains on a keratinous substrate at room temperature and atmospheric pressure for at least several hours, and that especially has a vapor pressure of less than $10^{-3}$ mmHg (0.13 Pa).

Exemplary non-volatile polar hydrocarbon-based oils usable in the context of embodiments of the present invention include, but are not limited to:

hydrocarbon-based polar oils such triglycerides consisting of fatty acid esters of glycerol, in particular the fatty acids of which may have chain lengths ranging from $C_4$ to $C_{36}$, and especially from $C_{18}$ to $C_{36}$, these oils possibly being linear or branched, and saturated or unsaturated; these oils may especially be heptanoic or octanoic triglycerides, wheatgerm oil, sunflower oil, grapeseed oil, sesame seed oil (820.6 g/mol), corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, *quinoa* oil, rye oil, safflower oil, candlenut oil, passionflower oil or musk rose oil; or alternatively caprylic/capric acid triglycerides, for instance those sold by the company Stéarineries Dubois or those sold under the tradenames Miglyol 810®, 812® and 818® by the company Dynamit Nobel;

synthetic ethers containing from 10 to 40 carbon atoms, such as dicaprylyl ether;

hydrocarbon-based (fatty) esters of formula $R_1COOR_2$ in which $R_1COO$ represents a carboxylic acid residue comprising from 2 to 40 carbon atoms, and $R_2$ represents a hydrocarbon-based chain containing from 1 to 40 carbon atoms, such as cetostearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, 2-ethylhexylhydroxysterate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, polyethylene glycol diheptanoate, propylene glycol 2-diethyl hexanoate, hexyl laurate, neopentanoic acid esters, for instance isodecyl neopentanoate, isotridecyl neopentanoate, isostearyl neopentanoate and 2-octyldodecyl neopentanoate, isononanoic acid esters, for instance isononyl isononanoate, isotridecyl isononanoate and octyl isononanoate, oleyl erucate, isopropyl lauroyl sarcosinate, diisopropyl sebacate, isocetyl stearate, isodecyl neopentanoate, isostearyl behenate, and myristyl myristate;

fatty alcohols containing from 12 to 26 carbon atoms, for instance octyldodecanol, 2-butyloctanol, 2-hexyldecanol, 2-undecylpentadecanol and oleyl alcohol;

higher $C_{12}$-$C_{22}$ fatty acids, such as oleic acid, linoleic acid and linolenic acid, and mixtures thereof;

fatty acids containing from 12 to 26 carbon atoms, for instance oleic acid;

dialkyl carbonates, the two alkyl chains possibly being identical or different, such as dicaprylyl carbonate sold under the trade name Cetiol CC® by Cognis; and aromatic esters such as tridecyl trimellitate, $C_{12}$-$C_{15}$ alcohol benzoate, 2-phenylethyl benzoate, and butyloctyl salicylate;

hydroxylated esters such as polyglycerol-2 triisostearate;

esters of $C_{24}$-$C_{28}$ branched fatty acids or fatty alcohols such as those described in EP Patent Application Publication No. 0955039, and especially triisoarachidyl citrate, pentaerythrityl tetraisononanoate, glyceryl triisostearate, glyceryl tris(2-decyl)tetradecanoate, pentaerythrityl tetraisostearate, polyglyceryl-2 tetraisostearate or pentaerythrityl tetrakis(2-decyl)tetradecanoate;

esters and polyesters of dimer diol and of monocarboxylic or dicarboxylic acid, such as esters of dimer diol and of fatty acid and esters of dimer diol and of dimer dicarboxylic acid, such as Lusplan DD-DA5® and Lusplan DD-DA7® sold by the company Nippon Fine Chemical and described in U.S. Patent Application Publication No. 2004/0175338, the content of which is incorporated into the present application by reference;

and any mixture of the foregoing.

In some embodiments, the oily substance is a fatty ester represented by the Formula $R_1COOR_2$ in which $R_1$ represents a linear or branched hydrocarbon-based chain comprising from 4 to 40 carbon atoms, preferably from 4 to 30 carbon atoms, more preferably from 7 to 20 carbon atoms, and $R_2$ represents a branched hydrocarbon-based chain containing from 3 to 40 carbon atoms, preferably from 10 to 30 carbon atoms, more preferably from 16 to 26 carbon atoms.

Exemplary such oily substances include, but are not limited to, isodecyl neopentanoate; isocetyl octanoate; isononyl isononanoate, isodecyl isononanoate, tridecyl isononanoate; hexyl laurate, 2-hexyldecyl laurate; isopropyl myristate, isocetyl myristate, isotridecyl myristate, 2-octyldodecyl myristate; isopropyl palmitate, 2-ethylhexyl palmitate, isooctyl palmitate, isocetyl palmitate, isodecyl palmitate, isostearyl palmitate, 2-octyldecyl palmitate; isopropyl isostearate, 2-ethylhexyl hydroxystearate, 2-octyldodecyl stearate, isostearyl isostearate; 2-octyldodecyl erucate; and mixtures thereof.

Preferred such oily substances include isodecyl neopentanoate; isocetyl octanoate; isononyl isononanoate; isopropyl isostearate, 2-ethylhexyl hydroxystearate, 2-octyldodecyl stearate, isostearyl isostearate; and mixtures thereof.

Additional exemplary oily substances usable in the context of these embodiments include, but are not limited to, triisodecyl trimellitate, dioctyl(2-ethylhexyl)carbonate, caprylyl carbonate (Cetiol CC), polyglyceryl-10 nonaisostearate, triisoarachidyl citrate, oxypropylenated (3 OP) myristyl diadipate, diethylhexyl adipate, propylene glycol dipelargonate, neopentyl glycol dicaprate, dipentaerythrityl hexacaprylate/hexacaprate, triisostearyl citrate, tri(2-ethylhexyl)trimellitate, glyceryl triisononanoate, 2-octyldodecyl hydroxystearate, dicaprylyl maleate, propylene glycol dioctanoate, caprylic/capric triglyceride, polyglyceryl-2 triisostearate, pentaerythrityl tetra(2-ethylhexanoate), triisocetyl citrate, diethylene glycol diisononanoate, glyceryl trioctanoate, tricaprylin, diisostearyl malate, glyceryl triheptanoate, dipropylene glycol dibenzoate, octyl hydroxystearate, 2-ethylhexyl palmitate glyceryl ether, propylene glycol monoisostearate, isostearyl lactate, polyglyceryl-2 diisostearate, oxyethylenated (7 OE) glyceryl triacetate, $C_{12-13}$ alkyl lactate, polyglyceryl-3 diisostearate, glyceryl triacetate, polyglyceryl-2 isostearate, octyl dodecanol, octyldodecyl neopentanoate, a caprylic/capric triglyceride, pentaerythrityl tetraisostearate, isodecyl neopentanoate, diisopropyl sebacate, and $C_{12}$-$C_{15}$ alkyl benzoate.

Exemplary plant oils usable as oily substance according to these embodiments include, but are not limited, castor oil, almond oil, wheat germ oil, jojoba oil, apricot oil, soya bean oil, canola oil.

In some embodiments, the oily substance is 2-ethylhexyl hydroxystearate, octyl hydroxystearate, ethylhexyl ethylhexanoate, castor oil, or any combination thereof.

In some embodiments, for the raw material used for making up the inner core of the microcapsule, when in a form of a dispersion of particles of the reflective agent in an oily substance, the weight of the reflective agent in the pre-dispersion (the raw material) ranges from 50% to 90%, or from 60% to 80%, or from 65% to 75% by weight of the total weight of the pre-dispersion. The weight of the oily substance is therefore in the range of from 10% to 50% by weight, or from 20% to 40% by weight, or from 25% to 35% by weight, of the total weight of the pre-dispersion, respectively.

In some embodiments, the weight ratio of the reflective agent particles and the oily substance ranges from 1.5:1 to 5:1, or from 1.5:1 to 3:1 or from 2:1 to 4:1, or from 2:1 to 3:1.

In exemplary embodiments, the reflective agent is bismuth chloride and the oily substance is 2-ethylhexyl hydroxystearate. In some of these embodiments, the raw material encapsulated in the microcapsules and forming the inner core is a product sold under the name of Biron® Liquid Silver or Timiron® Liquid Silver, by the company MERCK.

According to some embodiments of the present invention, the amount of the reflective agent or of a reflective agent and an oily substance, which constitute the inner core of the microcapsules, is within a range of from about 20% to about 90%, or from about 30% to about 90%, or from about 40% to about 90%, or from about 50% to about 90%, or from about 60% to about 90%, or from about 70% to about 90%, or from about 70% to about 80%, by weight, or from about 60% to about 80%, by weight, including any subranges and any intermediate values therebetween.

In some of any of the embodiments described herein, the microcapsule contains only one type of a reflective agent or a mixture of two or more reflective agents, either encapsulated individually, and/or one or more blends of reflective agents may be encapsulated within the inner core of the microcapsules. A person skilled in the art will know how to choose reflective agent and combinations of reflective agents to produce a desired effect on the skin.

The Wall-Forming Material:

The wall-forming material forms the outer shell(s) of the microcapsules of the present embodiments, and serves as a membrane for the encapsulated substance (the reflective agent). According to embodiments of the present invention, the wall forming material forming the outer shell(s) comprises a wall-forming polymer or co-polymer. In some of any of the embodiments of the present invention, one or more of the outer shells further comprise an opaque substance and/or a fatty acid salt, and may optionally further comprise a plasticizer.

The phrase "wall-forming polymer", which is also referred to herein as "wall-forming polymeric material" refers to a polymeric material (e.g., a polymer or copolymer) or a combination of two or more different polymeric materials, as defined herein, which form a component of the external wall or layer or shell of single-layer microcapsules, or, in the case of multi-layer microcapsules, additionally of the one or more intermediate shells between the inner core and the external (outer most) layer. In the context of single-layer microcapsules, the term "polymer shell" refers to a polymer layer comprised of the wall-forming polymer(s), which envelopes the inner core. In the context of multi-layer microcapsules, the term "polymer shell" refers to any of the polymer layers which envelopes the inner core, or which envelopes the preceding polymer layer.

In some embodiments, the wall-forming polymer is selected so as to sustain shear forces applied while being compounded in industrial processes, but, nevertheless, so as to provide microcapsule which are rupturable when applied (e.g., rubbed or pressed) on the skin.

In some embodiments, the wall-forming polymeric material comprises a polymer containing a sufficient amount of functional groups which are capable of forming hydrogen bonds.

In some embodiments, the polymeric material forming the one or more outer shells independently comprises hydrogen bond-forming functional groups featuring 4-40 weight percents of total polymer weight. Hydrogen bond-forming functional groups include, but are not limited to, functional groups which comprise one or more electron-donating atom(s) such as oxygen, sulfur and/or nitrogen.

In some embodiments, the hydrogen bond-forming groups include carboxylic acid, carboxylate, hydroxy, or any combination thereof.

In some embodiments, one or more, or each, of the wall-forming polymeric materials forming the outer shell(s) comprises a polyacrylate, a polymethacrylate, a cellulose ether or ester, or any combination thereof.

Exemplary wall-forming polymeric materials include, but are not limited to, polyacrylates, polymethacrylates, low molecular weight poly(methyl methacrylate)-co-(methacrylic acid) (e.g., 1:0.16), poly(ethyl acrylate)-co-(methyl methacrylate)-co-(trimethylammmonium-ethyl methacrylate chloride) (e.g., 1:2:0.1) (also known as Eudragit® RSPO), poly(butyl methacrylate)-co-(2-dimethylaminoethyl methacrylate)-co-(methyl methacrylate) (e.g., 1:2:1), poly(styrene)-co-(maleic anhydride), copolymer of octylacrylamide, cellulose ethers, cellulose esters, poly(ethylene glycol)-block-poly(propylene glycol)-block-poly(ethylene glycol), PLA (poly(lactic acid), PGA (poly(glycolide), PLGA (poly(lactide)-co-poly(glycolide) or any combination thereof.

Any combination of polymers and co-polymers as described herein is contemplated for a wall-forming material, as described herein.

In some embodiments, the wall-forming polymeric material of an outer shell comprises a cellulose ether or ester such as, but not limited to, methyl cellulose, ethyl cellulose, hydroxypropyl methyl cellulose, hydroxypropyl cellulose, cellulose acetate, cellulose acetate phthalate, cellulose acetate butyrate and hydroxypropyl methyl cellulose acetate phthalate. When a cellulose ether or ester is used in the polymeric material, it preferably contains about 4-20% hydroxyl groups which are free to form hydrogen bonds (e.g., hydroxyl groups which are not alkylated or acylated).

In some of any of the embodiments described herein, the wall-forming material of an outer shell comprises an acrylate/ammonium methacrylate copolymer such as, for example, Eudragit® RSPO. In some of any of the other embodiments of the present invention, the wall-forming material of an outer shell comprises a combination of the above-mentioned polymers such as, but not limited to, combinations of acrylate/ammonium methacrylate copolymer (e.g., Eudragit® RSPO) with either poly(methyl methacrylate), poly(methacrylate), poly(methyl methacrylate)-co-(methacrylic acid) or cellulose acetate.

When two polymeric materials are used as a wall-forming material, a weight ratio therebetween can range from 10:1 to 1:1, and can be, for example, 5:1, 4:1, 3:1, 2:1, or 3:2, including any intermediate values and subranges therebetween.

In some of any of the embodiments described herein, the wall forming material is or comprises poly(methyl methacrylate) (PMMA).

In some of any of the embodiments described herein, the wall forming material is or comprises a poly(methyl methacrylate)-co-(methacrylic acid) (PMMA/MA).

In some of any of the embodiments described herein, the wall forming material is or comprises an acrylate/ammonium methacrylate copolymer (e.g., Eudragit® RSPO).

In some of any of the embodiments described herein, the wall forming material is or comprises cellulose acetate.

The amount (weight/weight) of the wall-forming polymeric material(s) of the outer shell relative to the total microcapsule weight can be within a range of from about 5% to about 30%, or from about 5% to about 20%, or from about 5% to about 15%, or from about 5% to about 10%, by weight, including any subranges and any intermediate values therebetween.

In some embodiments, when the wall-forming material is a cellulose ester such as cellulose acetate, and the outer shell may not comprise a fatty acid salt, as described herein. In some such embodiments, the outer shell comprises an opaque substance, such as $TiO_2$, in an amount higher than 10%, by weight, for example, in an amount ranging from 20% to 40%, or from 30% to 40%, by weight, of the total weight of the microcapsule. In embodiments when the wall-forming material is cellulose acetate, the amount of the cellulose acetate can be, for example, from 5% to 10%, or from 5% to 8%, or about 5%, by weight, of the total weight of the composition.

In embodiments related to multi-layer microcapsules, the wall-forming material in each of the outer shells in the microcapsules described herein (e.g., a first wall-forming material of the inner core, a second wall-forming material of a first outer shell enveloping the inner core, and optionally a third wall-forming material of a second outer shell enveloping the first outer shell, and so forth) can be the same or different.

An Opaque Substance:

The outer shell of the single-layer microcapsules described herein can be opaque, semi-opaque or non-opaque (transparent). In some embodiments, the outer shell is opaque, and thus masks the light reflectance imparted by the reflective agent.

In some embodiments, one or more of the outer shells of multi-layer microcapsules as described herein can be opaque, semi-opaque or non-opaque (transparent). In some embodiments, one or more of the outer shells (e.g., the most outer shell) is opaque, and thus masks the light reflectance imparted by the reflective agent.

In some embodiments of the present invention, opacity of the outer shell of the microcapsules is obtained by an inclusion of an opaque substance.

As used herein, an "opaque substance" is a substance which is non-transparent and blocks at least 70% of the light passing therethrough.

Thus, an opaque outer shell blocks 70% to 100% of the light. Semi-opaque outer shell blocks up to 50% of the light. Non-opaque or transparent outer shell blocks no more than 30% of the light passing therethrough.

The terms "opacity" and "opaque" refer to herein to UV-vis light, such as, for example, daylight.

Exemplary opaque substances include, but are not limited to, $TiO_2$, zinc oxide, alumina, boron nitride, talc, mica and any combination thereof.

The total amount of opaque substances in the outer shell is within a range of from about 1% to about 50%, or from about 1% to about 40%, or from about 10% to about 40%, by weight, of the total weight of the microcapsule, including any subranges and any intermediate values therebetween.

In some of any of the embodiments described herein, the opaque substance is, or comprises, $TiO_2$, and in some embodiments, an amount of $TiO_2$ is within a range of from about 1% to about 30%, or from about 10% to about 40%, by weight, of the total weight of the microcapsule, including any subranges and any intermediate values therebetween.

In some of any of the embodiments described herein, the opaque substance is, or comprises, $TiO_2$, and in some embodiments, an amount of $TiO_2$ is about 10% by weight, of the total weight of the microcapsule.

In some of any of the embodiments described herein, the opaque substance is, or comprises, $TiO_2$, and in some embodiments, an amount of $TiO_2$ is about 35% by weight, of the total weight of the microcapsule.

In some embodiments, the outer shell does not comprise an opaque substance as described herein.

A Fatty Acid Salt:

In some of any of the embodiments described herein, an outer shell optionally comprises an opaque substance as described herein in any one of the respective embodiments, and/or alternatively, or in addition, further comprises a fatty acid salt as described herein in any one of the respective embodiments.

A fatty acid salt comprises a long hydrophobic hydrocarbon chain (e.g., of 4 to 30 carbon atoms in length) carboxylate anion (a fatty acyl) and a cation, as depicted in the following formula:

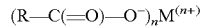

$$(R-C(=O)-O^-)_n M^{(n+)}$$

wherein R is a substituted or unsubstituted, liner or branched hydrocarbon chain of 4 to 30 carbon atoms, M+ is a cation, preferably a metal cation, and n is an integer representing the number of fatty acyls that interact with the cation, and also represents the charge number of the cation (e.g., 1, 2, 3, etc.).

The fatty acid salts that are usable in some of any of the embodiments of the present invention may contain 1 to 3 fatty acyl chains, each chain, independently, comprising 4 to 30 or 8 to 24 carbon atoms (C8-C24) in length. Thus, the fatty acid salt can be a salt of a monovalent, divalent or trivalent metal ion or a salt of an organic cation.

A monovalent metal ion can be, for example, $Na^+$, $K^+$, $Cs^+$, $Li^+$; a divalent metal ion is selected from $Mg^{2+}$, $Ca^{2+}$, Fe (II), $Co^{2+}$, $Ni^{2+}$, $Cu^{2+}$, $Mn^{2+}$, $Cd^{2+}$, $Sr^{2+}$ or $Zn^{2+}$; a thrivalent metal ion can be, for example, Fe(III), $La^{3+}$, $Eu^{3+}$ or $Gd^{3+}$; an organic cation can be, for example, ammonium, sulfonium, phosphonium or arsonium.

The fatty acyl can be derived from fatty acids such as, but not limited to, stearic acid, arachidic acid, palmitoleic acid, oleic acid, linoleic acid, linolaidic acid, arachidonic acid, myristoleic acid and erucic acid. Other fatty acids are also contemplated.

Exemplary fatty acid salts include, but are not limited to, magnesium stearate, magnesium oleate, calcium stearate, calcium linoleate, sodium stearate, magnesium arachidnoate, magnesium palmitate, magnesium linoleate, calcium arachidonoate, calcium myristoleate, sodium linoleate, calcium linoleate, sodium stearate, potassium stearate, sodium laurate, sodium myristate, sodium palmitate, potassium laurate, potassium myristate, potassium palmitate, calcium laurate, calcium myristate, calcium palmitate, zinc laurate, zinc myristate, zinc palmitate, zinc stearate, magnesium laurate, and magnesium myristate.

In some embodiments, the fatty acid salt is magnesium stearate.

The fatty acid salt is usually in an amount within a range of from about 0.05% to about 5%, or from about 0.1% to about 45%, or from about 0.2% to about 4%, or from about 0.5% to about 4%, or from about 0.5% to about 3.0%, or from about 0.75% to about 3.0%, or from about 1.0% to about 3.0%, or from about 1.0% to about 2.0%, or is about 1.0%, by weight, of the total microcapsule's weight, including any subranges and any intermediate values therebetween.

Without being bound by any particular theory, it is assumed that the cation of the fatty acid salt attracts the particles of an opaque substance and optionally the free carboxylic and/or hydroxyl groups of the wall-forming polymer, resulting in a better adhesion of both the opaque substance and the polymeric material to the inner core, thereby providing efficient masking of the reflective agent present in the inner core.

Fatty acid salts may be used in the preparation of single-layer microcapsules while being added to the organic phase together with the encapsulated material, and the wall-forming polymer, with or without the opaque substance. Upon contacting the organic phase with an aqueous phase, the fatty chains will spontaneously wrap around the encapsulated substance and their polar/ionic heads will interact with the oppositely charged opaque substance as well as with oppositely charged groups on the polymer, thereby enhancing the formation of an opaque polymeric envelope surrounding a core comprising the encapsulated material.

A Plasticizer:

In some embodiments of any of the embodiments of the present invention, an outer shell of the microcapsules further comprises a plasticizer.

Herein and in the art, a "plasticizer" describes a substance which increases the plasticity or fluidity of a composition. In the context of the present embodiments, a plasticizer is added to the wall-forming material in order to control the physical properties and level of elasticity of the microcapsule's outer shells.

Exemplary plasticizers include, but are not limited to, triethyl citrate, tricaprylin, trilaurin, tripalmitin, triacetin, acetyltriethyl citrate, paraffin oil, and any combination thereof. In exemplary embodiments, the plasticizer is triethyl citrate.

The amount of the plasticizer can be within a range of from about 0.5% to about 30%, or from about 0.5% to about 20%, or from about 1.0% to about 20%, or from about 5% to about 15%, or from about 5% to about 10%, or is about 10% by weight, of the total weight of the microcapsule, including any subranges and any intermediate values therebetween.

Microcapsules Composition:

According to an aspect of some embodiments of the present invention there is provided a composition which comprises a plurality of microcapsules, at least a portion of the microcapsules are microcapsules which comprise an inner core comprising a reflective agent, as described herein, and an outer shell (or two or more outer shells) comprised of a wall-forming polymeric material enveloping the inner core, as described in any one of the embodiments described herein.

In some embodiments, at least 10%, at least 20%, at least 30%, at least 40%, at least 50%, at least 60%, at least 70%, at least 80%, at least 90%, at least 95%, at least 98%, or at least 99%, or substantially all of the plurality of microcapsules in the composition are microcapsules as described in any one of the embodiments described herein.

A "composition" as used herein refers to a plurality of microcapsules, which can be the same or different, which, when different, can feature a plurality or variety of features. In accordance with embodiments of the present invention, at least a portion of the plurality of microcapsules exhibits all the technical features characterizing a reflective agent-encapsulating microcapsule as described herein, in any one of the embodiments thereof, for example, microcapsules encapsulating a reflective agent, optionally and preferably in combination with an oily substance, comprising a fatty acid salt, optionally comprising an opaque substance, and being breakable upon rubbing on the skin.

A "composition" as used in the context of these embodiments is a non-cosmetic composition, that is, the composition is not a cosmetic product or a cosmetic formulation. The composition, as used in the context of these embodiments, can be used as a raw material for making up a cosmetic product, composition or formulation.

According to an aspect of some embodiments of the present invention there is provided a plurality of microcapsules, at least a portion of the microcapsules are microcapsules which comprise an inner core comprising a reflective agent, as described herein, and an outer shell (or two or more outer shells) comprised of a wall-forming polymeric material enveloping the inner core, as described in any one of the embodiments described herein.

The plurality of microcapsules can also be referred to herein interchangeably as a mixture comprising a plurality of microcapsules.

In some embodiments, at least 10%, at least 20%, at least 30%, at least 40%, at least 50%, at least 60%, at least 70%, at least 80%, at least 90%, at least 95%, at least 98%, or at least 99%, or substantially all of the microcapsules in the plurality of microcapsules are microcapsules as described in any one of the embodiments described herein.

The term "at least a portion" means at least 20%, at least 50%, at least 70%, at least 60%, at least 80%, at least 90%, at least 95%, at least 98%, at least 99% or all of the microcapsules being the single-layer, core-shell reflective agent-encapsulating microcapsules, as described in any one of the respective embodiments herein.

In some embodiments, the plurality of microcapsules as described herein can be the same, or can differ from one another by, for example, the reflective agent encapsulated therein and/or the presence, absence or type of an oily substance in the inner core and/or the type of wall-forming polymeric material comprising the outer shell and/or by the presence or absence of an opaque substance and/or by the presence or absence of a fatty acid salt and/or by the number of outer shells.

In some embodiments related to the non-cosmetic composition or the plurality of microcapsules, a portion of the microcapsules can encapsulate a reflective agent as described herein, and another portion of the microcapsules can comprise a colorant, which is not a reflective agent as described herein, or another reflective agent, which is different by the type of the reflective agent and/or by the presence, absence or type of an oily substance in the inner core.

The terms "colorant", "color agent" and "pigment" are used herein interchangeably and refer to organic pigments such as synthetic or natural dyes selected from any of the well known FD&C or D&C dyes, inorganic pigments such as metal oxides, or lakes and any combination (blend) thereof. In some exemplary embodiments, the color agent is an inorganic pigment, such as, for example, a metal oxide.

The colorant may be oil-soluble or oil-dispersible or with limited solubility in water. Typically suitable colorants for microencapsulation according to some of any of the embodiments of the present invention include, but are not limited to, organic and inorganic pigments, lakes, natural and synthetic dyes and any combination thereof.

In some embodiments, the color agents are inorganic pigments such as, but not limited to, metal oxides such as iron oxides, titanium dioxide ($TiO_2$), titanium lower oxides, aluminum oxide, zirconium oxides, cobalt oxides, cerium oxides, nickel oxides, chromium oxide (chromium green), zinc oxide and composite metal oxides; metal hydroxides such as calcium hydroxide, iron hydroxides, aluminum hydroxide, chromium hydroxide, magnesium hydroxide and composite metal hydroxides; other colorants such as ferric ammonium ferrocyanide, Prussian blue, iron sulfides, manganese violet, carbon black, mica, kaolin, and any combination thereof.

In some of any of these embodiments, the inorganic pigments are selected from iron oxides, titanium dioxide, zinc oxide, chromium oxide/hydroxide, and mixtures thereof. In some embodiments, the color agent is iron oxide of any one of the three primary colors—red, yellow or black, or most preferably, a mixture thereof. Optionally, the colorant may comprise, besides the mixture of iron oxides, titanium dioxide, for the purpose of providing any desired final color or shade of color to the composition.

In some other embodiment, the colorants are Lake organic pigments produced by precipitation of a natural or synthetic dye with a metallic salt such as aluminum, calcium or barium salts. Such colorants are typically oil-dispersible and widely used in cosmetics. Examples of Lake pigments include, but are not limited to, Indigo Lakes, Carmine Lakes, lakes from the series of the well-known FD&C and D&C dyes such as D&C Red 21 Aluminum Lake, D&C Red 7 Calcium Lake.

As described herein, the colorant is included in the inner core of the microcapsules. Alternatively, a colorant can be included within an outer shell of microcapsules, either microcapsules encapsulating a reflective agent, as described herein, or other microcapsules in a composition as described herein.

In some of the embodiments described herein for a microcapsules-containing composition or mixture which consists of microcapsules containing a reflective agent as described herein, the average size of the microcapsules is within a range of from about 50 microns to about 400 microns, or from about 50 microns to about 300 microns, or from about 50 microns to about 200 microns, or from about 90 microns to about 200 microns, or from about 100 microns to about 200 microns, including any subranges and intermediate values therebetween.

In some of the embodiments described herein for a microcapsules-containing composition or mixture which consists of microcapsules encapsulating a reflective agent as described herein, the bulk density of the composition is within a range of from about 200 grams/Liter (or 0.2 gram/$cm^3$) to about 500 grams/Liter (or 0.5 gram/$cm^3$), or from about 250 grams/Liter (or 0.25 gram/$cm^3$) to about 450 grams/Liter (or 0.45 gram/$cm^3$), or from about 300 grams/

Liter (or 0.3 gram/cm$^3$) to about 400 grams/Liter (or 0.4 gram/cm$^3$), including any subranges and intermediate values therebetween.

Exemplary Compositions:

In some exemplary embodiments of the present invention, the microcapsules as described herein comprise, as the inner core, bismuth oxychloride pre-dispersed in 2-ethylhexyl hydroxystearate, or bismuth oxychloride and 2-ethylhexyl hydroxystearate.

In some of these embodiments, the amount of the inner core is at least 50%, by weight, of the total weight of the microcapsules or of the composition, and is, for example, 60%, or 70%, or 79%, or 80% of the total weight of the microcapsule or of the composition.

In some exemplary embodiments of the present invention, the microcapsules are single-layer microcapsules, and the outer shell comprises magnesium stearate in an amount within a range of from 1.0% to 2.0%, and TiO$_2$ in an amount within a range of from 5% to 15%, by weight, of the total weight of the microcapsule.

In some of these embodiments, the amount of the wall-forming material ranges from 5% to 15%, by weight, of the total weight of the composition.

In some of these embodiments, the wall-forming material comprises a poly (methyl methacrylate) or a copolymer of methyl methacrylic acid and acrylic acid or acrylate/ammonium methacrylate copolymer.

In some exemplary embodiments of the present invention, the microcapsules are single-layer microcapsules, and the outer shell comprises TiO$_2$ in an amount within a range of from 30% to 40%, by weight, of the total weight of the microcapsule, and does not comprise a fatty acid salt.

In some of these embodiments, the wall-forming material comprises a cellulose ester such as cellulose acetate.

In some exemplary embodiments, a microcapsule as described herein is a single-layer microcapsule and comprises a reflective agent as described herein in an amount of about 60-80% by weight, a wall-forming polymer or copolymer in an amount of 5-10% by weight, magnesium stearate in an amount of 0-1%, and TiO$_2$ in an amount of 0-35%, by weight.

In some exemplary embodiments of any of the embodiments described herein, at least most, or all, of the microcapsules in a composition are single-layer microcapsules, and in some of these embodiments, for at least most, or for all, of the microcapsules in the composition, the outer shell comprises magnesium stearate in an amount within a range of from 1.0% to 2.0%, by weight, TiO$_2$ in an amount within a range of from 1% to 20%, or from 5% to 15%, or in an amount of 10%, by weight, and, as a wall-forming material, PMMA, in an amount within a range of from 5% to 20%, or in an amount of 10%, by weight, of the total weight of the microcapsule or the composition. An exemplary such composition is presented in Example 1 hereinafter, and is characterized by a size distribution as presented in FIG. 1; bulk density of from 300 to 380 grams/liter (or from 0.30 to 0.38 gram/cm$^3$), and a masking effect reflected by a shift in the lightness, compared to the raw material, higher than 8. The amount of the raw material used to prepare the microcapsules is 79% by weight of the total weight of the composition.

In some exemplary embodiments of any of the embodiments described herein, at least most, or all, of the microcapsules in a composition are single-layer microcapsules, and in some of these embodiments, for at least most, or for all, of the microcapsules in the composition, the outer shell does not comprise magnesium stearate, and comprises TiO$_2$ in an amount within a range of 10% to 50%, or from 10% to 40%, or from 20% to 40%, or from 30% to 40%, or in an amount of 25%, by weight, and, as a wall-forming material, ethyl cellulose, in an amount within a range of 1% to 10%, or in an amount of 5%, by weight, of the total weight of the microcapsule or the composition. An exemplary such composition is presented in Example 2 hereinafter, and is characterized by a size distribution as presented in FIG. 2; bulk density of from 360 to 460 grams/Liter, and shift in the lightness, compared to the raw material, higher than 5. The amount of the raw material used to prepare the microcapsules is 60% by weight of the total weight of the composition.

In some exemplary embodiments of any of the embodiments described herein, at least most, or all, of the microcapsules in a composition are single-layer microcapsules, and in some of these embodiments, for at least most, or for all, of the microcapsules in the composition, the outer shell comprises magnesium stearate in an amount within a range of from 1.0% to 2.0%, by weight, TiO$_2$ in an amount within a range of 1% to 20%, or from 5% to 15%, or in an amount of 10%, by weight, and, as a wall-forming material, EUDRAGIT® RS PO (Poly(ethyl acrylate-co-methyl methacrylate-co-trimethyl ammonium ethyl methacrylate chloride), in an amount within a range of 5% to 20%, or in an amount of 10%, by weight, of the total weight of the microcapsule or the composition. An exemplary such composition is presented in Example 3 hereinafter, and is characterized by a size distribution as presented in FIG. 3; bulk density of from about 140 to about 360 grams/liter, and shift in the lightness, compared to the raw material, higher than 9. The amount of the raw material used to prepare the microcapsules is 79% by weight of the total weight of the composition.

In some exemplary embodiments of any of the embodiments described herein, at least most, or all, of the microcapsules in a composition are single-layer microcapsules, and in some of these embodiments, for at least most, or for all, of the microcapsules in the composition, the outer shell comprises magnesium stearate in an amount within a range of from 1.0% to 2.0%, by weight, TiO$_2$ in an amount within a range of 1% to 20%, or from 5% to 15%, or in an amount of 10%, by weight, and, as a wall-forming material, PMMA/MA, in an amount within a range of 5% to 20%, or in an amount of 10%, by weight, of the total weight of the microcapsule or the composition. An exemplary such composition is presented in Example 4 hereinafter. The amount of the raw material used to prepare the microcapsules is 79% by weight of the total weight of the composition.

In some exemplary embodiments of any of the embodiments described herein, at least most, or all, of the microcapsules in a composition are single-layer microcapsules, and in some of these embodiments, for at least most, or for all, of the microcapsules in the composition, the outer shell does not comprise magnesium stearate nor TiO$_2$, and comprises a plasticizer, in an amount within a range of 1% to 20%, or from 5% to 15%, or in an amount of 10%, by weight, and, as a wall-forming material, EUDRAGIT® RS PO (Poly(ethyl acrylate-co-methyl methacrylate-co-trimethyl ammonium ethyl methacrylate chloride), in an amount within a range of 5% to 20%, or in an amount of 10%, by weight, of the total weight of the microcapsule or the composition. An exemplary such composition is presented in Example 5 hereinafter, and is characterized by a size distribution as presented in FIG. 4; bulk density of from about 440 to about 540 grams/liter, and shift in the lightness, compared to the raw material, higher than 13. The amount of the raw material used to prepare the microcapsules is 80% by weight of the total weight of the composition.

The Process:

The process used for the preparation of the microcapsules according to embodiments of the present invention is a modification of the microencapsulation solvent removal method disclosed, for example, in U.S. Pat. Nos. 6,932,984 and 7,838,037 and WO 2012/156965, which are incorporated by reference as if fully set forth herein. According to this technology, the active ingredient is found in the core of the microcapsule. This technique seals each micro-capped ingredient from chemical and cross-link reactions, degradation, color change or loss of potency during production, and for extended periods in storage.

The solvent removal process is based on four main steps as follows:

(i) preparing a homogeneous organic solution comprising the encapsulated agent, and a wall-forming polymeric material, and optionally an opaque substance and/or a fatty acid salt, and an organic solvent that is partially miscible in water;

(ii) preparing an emulsion of an aqueous continuous phase containing an emulsifier and saturated with the same organic solvent of the organic solution, and optionally comprising the opaque substance;

(iii) mixing the homogeneous organic solution with the aqueous emulsion, under high shear stirring to thereby form an emulsion; and (iv) extracting the organic solvent by adding to the emulsion formed in step (iii) an amount of water which initiates extraction of the organic solvent from the emulsion, thereby obtaining the microcapsules.

For multi-layer (e.g., double-layer and triple-layer) microcapsules, the microcapsules are formed by first modifying the surface of the single-layer microcapsules formed according to steps (i)-(iv) and then subjecting the surface-modified inner core microcapsules to one or more cycles of steps (i)-(iv), when the inner core microcapsules are dispersed in the organic solution together with the wall-forming material.

In some embodiments, the microcapsules according to the present embodiments can be prepared a modified solvent removal method comprising the following steps:

(a) contacting an organic phase comprising a reflective agent, and a wall-forming polymer or copolymer, optionally a fatty acid salt, and optionally an opaque substance and/or a plasticizer, and a first partially water-miscible organic solvent, with an aqueous solution saturated with said organic solvent and comprising an emulsifier, to thereby obtain an emulsion; and (b) adding to the formed emulsion an amount of water which initiates extraction of the organic solvent from the emulsion, thereby obtaining the microcapsules.

In further steps, the microcapsules are isolated following step (b), dried and sifted to thereby obtain a free flowing powder of the microcapsules.

These steps are further detailed as follows:

The homogenous solution prepared in step (a) is obtained by preparing an organic solution or dispersion of a wall-forming polymeric material as described in any one of the respective embodiments described herein, in an organic solvent that is partially miscible in water and is capable of dissolving or dispersing the wall-forming polymer. In exemplary embodiments, the organic solvent is an organic solvent approved for topical applications, such as, but not limited to, ethyl acetate, ethanol, ethyl formate, or any combination thereof. In some embodiments, the organic solvent is ethyl acetate.

The fatty acid salt is as described in any one of the respective embodiments described herein. The opaque substance is as described in any one of the respective embodiments described herein. In preferred embodiments, the opaque substance is $TiO_2$.

When a plasticizer is used, it is usually selected from tricaprylin, trilaurin, tripalmitin, triacetin, triethyl citrate, acetyltriethyl citrate, paraffin oil, or any combination thereof.

The components of the organic solution are mixed/stirred until a homogeneous, optionally transparent, solution or dispersion is obtained.

The aqueous continuous phase is saturated with the organic solvent that forms the organic solution, and typically comprises an emulsifier, and optionally the opaque substance (if included in the microcapsule and not included in the organic phase).

The organic solution or dispersion and the aqueous continuous phase are mixed under low sheer stirring to thereby form an emulsion.

In step (b), an amount of water is added to the emulsion prepared in (a), thereby extracting the organic solvent and allowing the r microcapsules to form.

In the context of embodiments of the invention, the term "low sheer stirring" refers to a mixing at about 100-800 rpm, preferably at about 300-600 rpm.

In some embodiments, when the microcapsules are multi-layer microcapsules, the process further comprises: (c) optionally repeating steps (a) and (b), using a second, third, and so on, organic phases and aqueous continuous phases, thereby obtaining multi-layered microcapsules.

Topical Formulations:

As discussed hereinabove, the reflective agent-encapsulating microcapsules as described herein are particularly usable for inclusion in topical formulations, particularly cosmetic or cosmeceutical formulations and products.

In some embodiments, the composition provided herein is used in cosmetic, cosmeceutical or pharmaceutical formulations such as skin care formulations, make-up or dermatological or other topical pharmaceutical formulations, comprising the microcapsules as described herein (e.g., a color composition as described herein). The formulation can optionally and preferably further comprise a carrier, and optionally additional active agents and/or additives.

As used herein a "formulation" refers to a vehicle in the form of emulsion, lotion, cream, gel, powder, etc., that comprises the reflective agent-encapsulating microcapsules as described herein with physiologically acceptable carriers and excipients and optionally other chemical components such as cosmetic, cosmeceutical or pharmaceutical agents (e.g., drugs).

As used herein, the term "physiologically acceptable" means approved by a regulatory agency of the Federal or a state government or listed in the U.S. Pharmacopeia or other generally recognized pharmacopeia for use in animals, and more particularly in humans.

Herein, the phrase "physiologically suitable carrier" refers to an approved carrier or a diluent that does not cause significant irritation to an organism and does not abrogate the biological activity and properties of a possible active agent.

Herein the term "excipient" refers to an inert substance added to a pharmaceutical composition to further facilitate processes and administration of the active ingredients.

In some embodiment of the present invention, the cosmetic or cosmeceutical formulation is formulated in a form suitable for topical application on the applied area (e.g., facial skin).

By selecting the appropriate carrier and optionally other ingredients that can be included in the composition, as is detailed hereinbelow, the compositions of the present embodiments may be formulated into any form typically employed for topical application.

By "appropriate carrier" for topical application it is meant any medium compatible with a keratinous substrate, which has a color, a smell and a pleasant feel and which does not generate unacceptable discomfort (stinging, tautness or redness).

The phrase "keratinous material" or "keratinous substrate" means, in some embodiments of the present invention, the skin and especially areas like the face, cheeks, hands, body, legs, around the eyes, the eyelids and the lips.

The formulations can be water-based, oil-based, emulsion-based (including water-in-oil, oil-in-water, water-in-oil-in-water and oil-in-water-in-oil emulsions) or silicon-based.

The formulations as described herein can be, for example, skin care products, make-up products (including eye shadows, make-up, lipstick, lacquer, etc., or any other product as described herein).

In some embodiments, a formulation as described is in a form of a cream, an ointment, a paste, a gel, a lotion, a milk, an oil, a suspension, a solution, an aerosol, a spray, a foam, a powder (e.g., a pressed powder or a loose powder) or a mousse.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in *Remington: The Science and Practice of Pharmacy,* 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the sunscreens-containing microcapsules, are present in a water or alcohol base. Lotions are typically preferred for covering/protecting large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to *Remington: The Science and Practice of Pharmacy,* supra, for further information.

Pastes are semisolid dosage forms in which the bioactive agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base. Additional reference may be made to *Remington: The Science and Practice of Pharmacy,* for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

The preparation of the formulation can be carried out by mixing and homogenizing all the ingredients except for the reflective agent-encapsulating microcapsules, and adding the reflective-agent encapsulating microcapsules at the end, followed by low shear mixing of the mixture.

The reflective agent-encapsulating microcapsules of the invention can be used in pharmaceutical compositions for topical application, which include, for example, pharmaceutically active agents for dermatological or transdermal applications.

In any of the formulations described herein, additional agents and/or additives can be included. These agents and/or additives and can be encapsulated or non-encapsulated.

In some embodiments, one or more of these agents and/or additives is encapsulated.

In some of these embodiments, the agents and/or additives are encapsulated using microcapsules as described in any one of U.S. Pat. Nos. 6,932,984 and 7,838,037, and WO 2009/138978.

Some non-limiting representative examples of additives and/or agents include humectants, deodorants, antiperspirants, sunscreen agents (e.g., UV blocking agents, UV filters), sunless tanning agents, hair conditioning agents, pH adjusting agents, chelating agents, preservatives, emulsifiers, occlusive agents, emollients, thickeners, solubilizing agents, penetration enhancers, anti-irritants, colorants, propellants and surfactants.

Representative examples of humectants include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propyleneglycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

Suitable pH adjusting agents include, for example, one or more of adipic acids, glycines, citric acids, calcium hydroxides, magnesium aluminometasilicates, buffers or any combinations thereof.

Representative examples of deodorant agents include, without limitation, quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmlthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above.

Antiperspirant agents can be incorporated in the compositions of the present invention either in a solubilized or a particulate form and include, for example, aluminum or zirconium astringent salts or complexes.

Representative examples of sunless tanning agents include, without limitation, dihydroxyacetone, glyceraldehyde, indoles and their derivatives. The sunless tanning agents can be used in combination with the sunscreen agents.

The chelating agents are optionally added to formulations so as to enhance the preservative or preservative system. Preferred chelating agents are mild agents, such as, for example, ethylenediaminetetraacetic acid (EDTA), EDTA derivatives, or any combination thereof.

Suitable preservatives include, without limitation, one or more alkanols, disodium EDTA (ethylenediamine tetraacetate), EDTA salts, EDTA fatty acid conjugates, isothiazolinone, parabens such as methylparaben and propylparaben, propyleneglycols, sorbates, urea derivatives such as diazolindinyl urea, or any combinations thereof.

Suitable emulsifiers include, for example, one or more sorbitans, alkoxylated fatty alcohols, alkylpolyglycosides, soaps, alkyl sulfates, monoalkyl and dialkyl phosphates, alkyl sulphonates, acyl isothionates, or any combinations thereof.

Suitable occlusive agents include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Suitable emollients include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids and their alkali salts and mixtures thereof.

Representative examples of solubilizing agents that are usable in this context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEENS and spans, e.g., TWEEN 80. Other solubilizers that are usable for the compositions of the present invention are, for example, polyoxyethylene sorbitan fatty acid ester, polyoxyethylene n-alkyl ethers, n-alkyl amine n-oxides, poloxamers, organic solvents, phospholipids and cyclodextrines.

Suitable penetration enhancers include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propyleneglycol (PG), propyleneglycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil. Such oils include, for example, safflower oil, cottonseed oil and corn oil.

Suitable anti-irritants include, for example, steroidal and non steroidal anti-inflammatory agents or other materials such as aloe vera, chamomile, alpha-bisabolol, cola *nitida* extract, green tea extract, tea tree oil, licoric extract, allantoin, caffeine or other xanthines, glycyrrhizic acid and its derivatives.

Exemplary additional active agents according to these embodiments of present invention include, without limitation, one or more, or any combination of an antibiotic agent, an antimicrobial agent, an anti-acne agent, an anti-aging agent, a wrinkle-reducing agent, a skin whitening agent, a sebum reducing agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an anti-oxidant, an antineoplastic agent, an immunomodulator, an interferon, an antidepressant, an anti histamine, a vitamin, a hormone and an anti-dandruff agent.

In some of any of the embodiments described herein, a topical formulation comprises, in addition to the microcapsules encapsulating a reflective agent as described herein, an additional agent, as described herein, which is encapsulated. In some of these embodiments, the topical formulation comprises an additional type of microcapsules, which encapsulate the additional agent. In some of these embodiments, the additional type of microcapsules is selected as being compatible with the microcapsules encapsulating a reflective agent as described herein.

Exemplary such microcapsules are microcapsules as described in U.S. Pat. Nos. 6,932,984 and 7,838,037 and WO 2012/156965. More specific examples include microcapsules marketed by Tagra, under the tradenames Tagra-Cap1™, TagraCap3™ and CameleonCaps™, for colorant-encapsulating microcapsules; SunCaps™, for UV filter-encapsulating microcapsules; Tagravit™ for vitamin-encapsulating microcapsules; and Tagrol™, for essential oil-encapsulating microcapsules.

It is expected that during the life of a patent maturing from this application many relevant reflective agents, wall-forming materials and opaque substances will be developed and the scope of the term "reflective agent", "wall-forming polymer" and "opaque substance" is intended to include all such new technologies a priori.

As used herein the term "about" refers to ±10% or to ±5% or to ±1%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Ethyl acetate was obtained from Gadot, Israel.

Magnesium stearate was obtained from FACI ASIA PACIFIC PTE Ltd.

Titanium oxide, which is also referred to herein throughout as titanium dioxide or $TiO_2$ RC402, was obtained from Sachtleben Chemie GmbH.

Bismuth oxychloride pre-dispersed 2-ethylhexyl hydroxystearate (marketed as Timiron® Liquid Silver) was obtained from Merck KGaA, Darmstadt, Germany.

Polyvinyl alcohol (PVA) as used was Mowiol 4-88, KSE solution 4%; Kuraray America, Inc., USA.

Cellulose acetate 398-10NF was obtained from Eastman, USA.

(Poly(ethyl acrylate-co-methyl methacrylate-co-trimethylammonium ethyl methacrylate chloride), EUDRAGIT® RS PO, was obtained from Evonik industries, Germany).

Size distribution of the microcapsules was determined using HORIBA LA300.

Loose Bulk Density of the microcapsules was determined using USP-NF <616>.

Example 1

Preparation of PMMA Microcapsules Containing Bismuth Oxychloride Predispersed 2-Ethylhexyl Hydroxystearate 1.1 Preparation of Organic Phase/Master Batch (MB)

An organic phase (herein referred to interchangeably as "master batch" (MB)) was prepared by gradually adding 10 grams of the wall-forming polymer poly(methyl methacrylate) (PMMA) under stirring (10 minutes), into 300 grams of ethyl acetate, heating the obtained mixture to 50° C. and stirring well until the mixture was homogeneous and transparent (about 20 minutes). The obtained polymer solution was cooled to 25° C. One gram of Magnesium Stearate (MgSt) was added to the solution under stirring for about 5 minutes. Ten grams of Titanium dioxide ($TiO_2$) were then added to the solution under stirring for about 5 minutes and then the mixture was homogenized for about 8 minutes.

A mixture of bismuth oxychloride predispersed 2-ethylhexyl hydroxystearate (79 grams) was added to the previous suspension under stirring for about 5 minutes.

A list of the components included in the prepared MB is presented in Table 1.

TABLE 1

| Master batch constituents | |
|---|---|
| Material | Loading for 100 grams MB |
| poly(methyl methacrylate) | 10.0 |
| $TiO_2$ RC402 | 10.0 |
| Magnesium stearate | 1.0 |
| Bismuth oxychloride predispersed 2-ethylhexyl hydroxystearate | 79.0 |
| Ethyl acetate | 300.0 |

1.2 Preparation of the Emulsion

An aqueous solution of 0.25% polyvinyl alcohol (PVA) was prepared by mixing water (1013 grams) with PVA 4% solution (68 grams). Ethyl acetate (120 grams) was added to the aqueous solution, and the master batch of step 1.1 above was thereafter gradually added into the ethyl acetate/water emulsion under stirring at about 400 RPM for 2 minutes. The ratio between the master batch and the emulsion (w/w) was 1:3. A list of the components included in the prepared emulsion is presented in Table 2.

TABLE 2

| Emulsion constituents | |
|---|---|
| Material | Loading (grams) |
| Water | 1013 |
| PVA (4% solution) | 68 |
| Ethyl Acetate | 120 |
| MB | 400 |

1.3 Extraction of the Organic Solvent

The extraction solution was composed of a mixture of 8775 grams water and 225 grams of PVA solution 4% (final concentration of PVA in the extraction solution was 0.10% PVA). The emulsion of step 1.2 above (1600 grams) was gradually added into the extraction solution in a 15 L pail under stirring at 150 RPM using a manual pump, and the obtained mixture was further stirred for additional 15 minutes. The resulting mixture was left to sediment for about 24 hours at 25° C. A list of the components included in extraction medium is presented in Table 3.

TABLE 3

| Extraction medium constituents | |
|---|---|
| Material | Loading (grams) |
| Emulsion | 1600 |
| Water | 8775 |
| 4% PVA solution | 225 |

1.4 Washing, Drying and Sifting of the Microcapsules

The microcapsules obtained in step 1.3 above were separated either by sedimentation or vacuum filtration, and then dried and sifted.

In the sedimentation procedure, the upper liquid phase from the pail was decanted and the remaining suspension was shaken and transferred to a drying vessel.

In the filtration procedure, the upper phase liquid was decanted from the pail, the remaining suspension was shaken and then filtered, and the sediment was rinsed on the filter with 400 ml water. The suspension was transferred to a drying vessel.

In the drying stage, the microcapsules were freeze dried (lyophilized) for 48 hours.

In the sifting stage, the dried microcapsules were sifted using automatic sifter "Ari j-Levy", Sifter MIC. 100. The sifted microcapsules were stored in an appropriate container at room temperature or in a refrigerator.

Example 2

Preparation of Cellulose Acetate Microcapsules Containing Bismuth Oxychloride Predispersed 2-Ethylhexyl Hydroxystearate 2.1 Preparation of Organic Phase/Master Batch (MB) Stage An organic phase (herein referred to interchangeably as "master batch" (MB)) was prepared by gradually adding 5 grams of the wall-forming polymer Cellulose Acetate 398-10NF (CA) under stirring (10 minutes), into 300 grams of ethyl acetate, and stirring the obtained mixture until the mixture was homogeneous and transparent (about 20 minutes). Thirty grams of Titanium dioxide ($TiO_2$) were then added to the obtained solution under stirring for about 5 minutes and then the mixture was homogenized for about 8 minutes. A mixture of bismuth oxychloride predispersed in 2-ethylhexyl hydroxystearate (60 grams) was thereafter added to the suspension under stirring for about 5 minutes.

A list of the components included in the prepared MB is presented in Table 4.

TABLE 4

Master batch constituents

| Material | Loading for 100 grams MB |
| --- | --- |
| Cellulose acetate 398-10NF | 5.0 |
| TiO$_2$ RC402 | 35.0 |
| Bismuth oxychloride predispersed 2-ethylhexyl hydroxystearate | 60.0 |
| Ethyl acetate | 300.0 |

2.2 Preparation of the Emulsion

An aqueous solution of 0.4% polyvinyl alcohol (PVA) was prepared by mixing water (972 grams) with PVA 4% solution (108 grams). Ethyl acetate (120 grams) was added to the aqueous phase, and the master batch of step 3.1 above was thereafter gradually added into the ethyl acetate/water emulsion under stirring at about 400 RPM for 2 minutes. The ratio between the master batch and the emulsion (w/w) was 1:3. A list of the components included in the prepared emulsion is presented in Table 5.

TABLE 5

Emulsion constituents

| Material | Loading (grams) |
| --- | --- |
| Water | 972 |
| PVA (4% solution) | 108 |
| Ethyl Acetate | 120 |
| MB | 400 |

2.3 Extraction of the Organic Solvent

The extraction solution was composed of a mixture of 8550 grams water and 450 grams of PVA solution 4% (final concentration of PVA in the extraction fluid 0.20% PVA). The emulsion of step 3.2 above (1600 grams) was gradually added to the extraction solution in a 15 L pail under stirring at 150 RPM using a manual pump, and the obtained mixture was further stirred for additional 15 minutes. The resulting mixture was left to sediment for about 24 hours at 25° C. A list of the components included in the prepared extraction medium is presented in Table 6.

The components of the extraction medium are presented in Table 6.

TABLE 6

Extraction medium constituents

| Material | Loading (grams) |
| --- | --- |
| Emulsion | 1600 |
| Water | 8550 |
| 4% PVA solution | 450 |

2.4 Washing, Drying and Sifting of the Microcapsules

The microcapsules obtained in step 3.3 above were separated either by sedimentation or vacuum filtration, dried and sifted, as described hereinabove, for Example 1.

Example 3

Preparation of EUDRAGIT® Microcapsules Containing Bismuth Oxychloride Predispersed 2-Ethylhexyl Hydroxystearate

3.1 Preparation of Organic Phase/Master Batch (MB) Stage

An organic phase (herein referred to interchangeably as "master batch" (MB)) was prepared by gradually adding 10 grams of the wall-forming Poly(ethyl acrylate-co-methyl methacrylate-co-trimethylammonioethyl methacrylate chloride) (EUDRAGIT® RS PO) under stirring (10 minutes), into 300.0 grams of ethyl acetate, heating to 50° C. and stirring well until the mixture was homogeneous and transparent (about 20 minutes). The obtained polymer solution was cooled to 25° C. One gram of Magnesium Stearate (MgSt) was added to the solution under stirring for about 5 minutes. Then, bismuth oxychloride predispersed 2-ethylhexyl hydroxystearate (79 grams) was added to the suspension under stirring for about 5 minutes.

The components of the MB are presented in Table 7.

TABLE 7

Master batch constituents

| Material | Loading for 100 grams MB |
| --- | --- |
| EUDRAGIT ® RS PO (Poly(ethyl acrylate-co-methyl methacrylate-co-trimethylammonioethyl methacrylate chloride) | 10.0 |
| Magnesium Stearate | 1.0 |
| Bismuth oxychloride predispersed 2-ethylhexyl hydroxystearate | 79.0 |
| Ethyl acetate | 233 |

3.2 Preparation of the Emulsion

An aqueous solution of 0.25% polyvinyl alcohol (PVA) was prepared by mixing water (844 grams) with PVA 4% solution (56 grams). Ethyl acetate (100 grams) was added to the water phase. Ten grams of Titanium dioxide (TiO$_2$) was added to previous step under stirring for about 5 minutes and then the mixture was homogenized for about 8 minutes and then the master batch of step 4.1 above was gradually added into the ethyl acetate/water emulsion under stirring at about 400 RPM for 2 minutes. The ratio between the master batch and the emulsion (w/w) was 1:3. The components of the emulsion are presented in Table 8.

TABLE 8

Emulsion constituents

| Material | Loading (grams) |
| --- | --- |
| Water | 844 |
| PVA (4% solution) | 56 |
| Ethyl Acetate | 100 |
| TiO$_2$ RC402 | 10 |
| MB | 323 |

3.3 Extraction of the Organic Solvent

The extraction fluid was composed of a mixture of 6923 grams water and 178 grams of PVA solution 4% (final concentration of PVA in the extraction fluid 0.10% PVA). The emulsion of step 4.2 above (1333 grams) was gradually added into the extraction fluid in a 15 L pail under stirring at 150 RPM using a manual pump, and was further stirred for additional 15 minutes. The resulting mixture was left to sediment for about 24 hours at 25° C. The components of the extraction medium are presented in Table 9.

TABLE 9

Extraction medium constituents

| Material | Loading (grams) |
|---|---|
| Emulsion | 1333 |
| Water | 6923 |
| 4% PVA solution | 178 |

3.4 Washing, Drying and Sifting of the Microcapsules

The microcapsules obtained in step 3.3 above were separated either by sedimentation or vacuum filtration, dried and sifted, as described hereinabove, for Example 1.

Example 4

Preparation of PMMA/MA Microcapsules Containing Bismuth Oxychloride Predispersed 2-Ethylhexyl Hydroxystearate 4.1 Preparation of Organic Phase/Master Batch (MB) Stage An organic phase (herein referred to interchangeably as "master batch" (MB)) was prepared by gradually adding 10 grams of the wall-forming polymer Poly(methacrylic acid-co-methyl methacrylate) (PMMA/MA) under stirring (10 minutes), into 300.0 grams of ethyl acetate, heating to 50° C. and stirring well until the mixture was homogeneous and transparent (about 20 minutes). The obtained polymer solution was cooled to 25° C. One gram of Magnesium Stearate (MgSt) was added to the solution under stirring for about 5 minutes. Ten grams of Titanium dioxide (TiO$_2$) were thereafter added under stirring for about 5 minutes and then the mixture was homogenized for about 8 minutes. Thereafter, bismuth oxychloride predispersed 2-ethylhexyl hydroxystearate (79 grams) was added to the suspension under stirring for about 5 minutes.

The components of the MB are presented in Table 10.

TABLE 10

Master batch constituents

| Material | Loading for 100 grams MB |
|---|---|
| Poly(methacrylic acid-co-methyl methacrylate) (PMMA/MA) | 10.0 |
| TiO$_2$ RC402 | 10.0 |
| Magnesium stearate | 1.0 |
| Bismuth oxychloride predispersed 2-ethylhexyl hydroxystearate | 79.0 |
| Ethyl acetate | 300.0 |

4.2 Preparation of the Emulsion

An aqueous solution of 0.25% polyvinyl alcohol (PVA) was prepared by mixing water (1013 grams) with PVA 4% solution (68 grams). Ethyl acetate (120 grams) was added to the water phase, and then the master batch of step 1.1 above was gradually added into the ethyl acetate/water emulsion under stirring at about 400 RPM for 2 minutes. The ratio between the master batch and the emulsion (w/w) was 1:3. The components of the emulsion are presented in Table 11.

TABLE 11

Emulsion constituents

| Material | Loading (grams) |
|---|---|
| Water | 1013 |
| PVA (KSE 4% solution) | 68 |
| Ethyl Acetate | 120 |
| MB | 400 |

4.3 Extraction of the Organic Solvent

The extraction fluid was composed of a mixture of 8775 grams water and 225 grams of PVA solution 4% (final concentration of PVA in the extraction fluid 0.10% PVA). The emulsion of step 1.2 above (1600 grams) was gradually added into the extraction fluid in a 15 L pail under stirring at 150 RPM using a manual pump, and was further stirred for additional 15 minutes. The resulting mixture was left to sediment for about 24 hours at 25° C. The components of the extraction medium are presented in Table 12.

TABLE 12

Extraction medium constituents

| Material | Loading (grams) |
|---|---|
| Emulsion | 1600 |
| Water | 8775 |
| 4% PVA solution | 225 |

4.4 Washing, Drying and Sifting of the Microcapsules

The microcapsules obtained in step 4.3 above were separated either by sedimentation or vacuum filtration, dried and sifted, as described hereinabove, for Example 1.

Example 5

Preparation of EUDRAGIT® Microcapsules Containing Bismuth Oxychloride Predispersed 2-Ethylhexyl Hydroxystearate 5.1 Preparation of Organic Phase/Master Batch (MB) Stage An organic phase (herein referred to interchangeably as "master batch" (MB)) was prepared by gradually adding 10 grams of the wall-forming polymer Poly(ethyl acrylate-co-methyl methacrylate-co-trimethylammonioethyl methacrylate chloride) (EUDRAGIT® RS PO) under stirring (10 minutes), into 185.7 grams of ethyl acetate, heating to 50° C. and stirring well until the mixture was homogeneous and transparent (about 20 minutes). The obtained polymer solution was cooled to 25° C. Ten grams of Triethyl Citrate were added to the solution under stirring for about 5 minutes. Eighty grams of bismuth oxychloride (BiClO) were thereafter added to the mixture under stirring for about 5 minutes and then the mixture was homogenized for about 8 minutes.

The components of the MB are presented in Table 13.

TABLE 13

Master batch constituents

| Material | Loading for 100 grams MB |
|---|---|
| EUDRAGIT ® RS PO (Poly(ethyl acrylate-co-methyl methacrylate-co-trimethylammonioethyl methacrylate chloride) | 10.0 |

TABLE 13-continued

| Master batch constituents | |
|---|---|
| Material | Loading for 100 grams MB |
| Triethyl Citrate | 10.0 |
| Bismuth oxychloride | 80.0 |
| Ethyl acetate | 185.7 |

5.2 Preparation of the Emulsion

An aqueous solution of 0.25% polyvinyl alcohol (PVA) was prepared by mixing water (723.2 grams) with PVA 4% solution (48.2 grams). Ethyl acetate (85.7 grams) was added to the water phase, and then the master batch of step 6.1 above was gradually added into the ethyl acetate/water emulsion under stirring at about 400 RPM for 10 minutes. The ratio between the master batch and the emulsion (w/w) was 1:3. The components of the emulsion are presented in Table 14.

TABLE 14

| Emulsion constituents | |
|---|---|
| Material | Loading (grams) |
| Water | 723.2 |
| PVA (4% solution) | 48.2 |
| Ethyl Acetate | 85.7 |
| MB | 285.7 |

5.3 Extraction of the Organic Solvent

The extraction fluid was composed of a mixture of 5599 grams water and 144 grams of PVA solution 4% (final concentration of PVA in the extraction fluid 0.10% PVA). The emulsion of step 6.2 above (1449.2 grams) was gradually added into the extraction fluid in a 15 L pail under stirring at 150 RPM using a manual pump, and was further stirred for additional 15 minutes. The resulting mixture was left to sediment for about 24 hours at 25° C. The components of the extraction medium are presented in Table 15.

TABLE 15

| Extraction medium constituents | |
|---|---|
| Material | Loading (grams) |
| Emulsion | 1449.2 |
| Water | 5599 |
| 4% PVA solution | 144 |

5.4 Washing, Drying and Sifting of the Microcapsules

The microcapsules obtained in step 5.3 above were separated either by sedimentation or vacuum filtration, dried and sifted, as described hereinabove, for Example 1.

Example 6

Characterization

Figure 2:
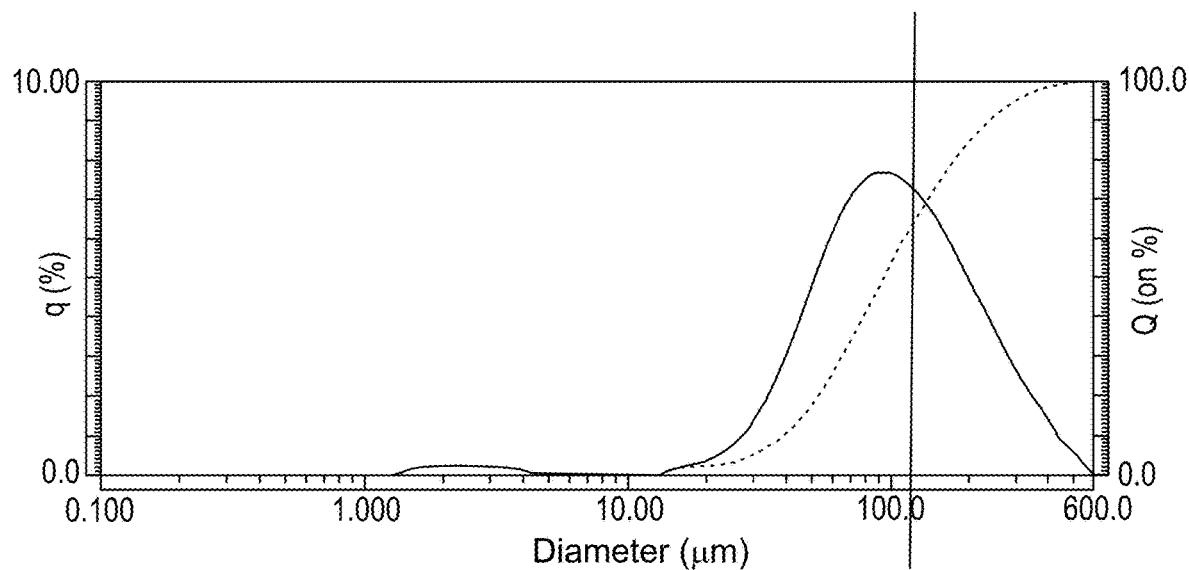
Figure 3:
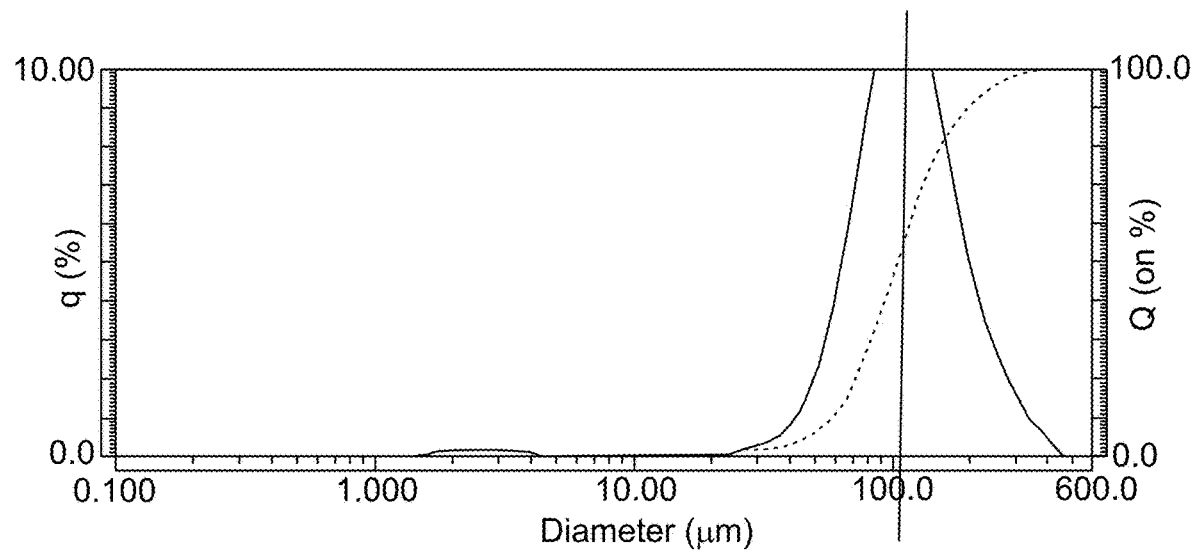
Figure 4:
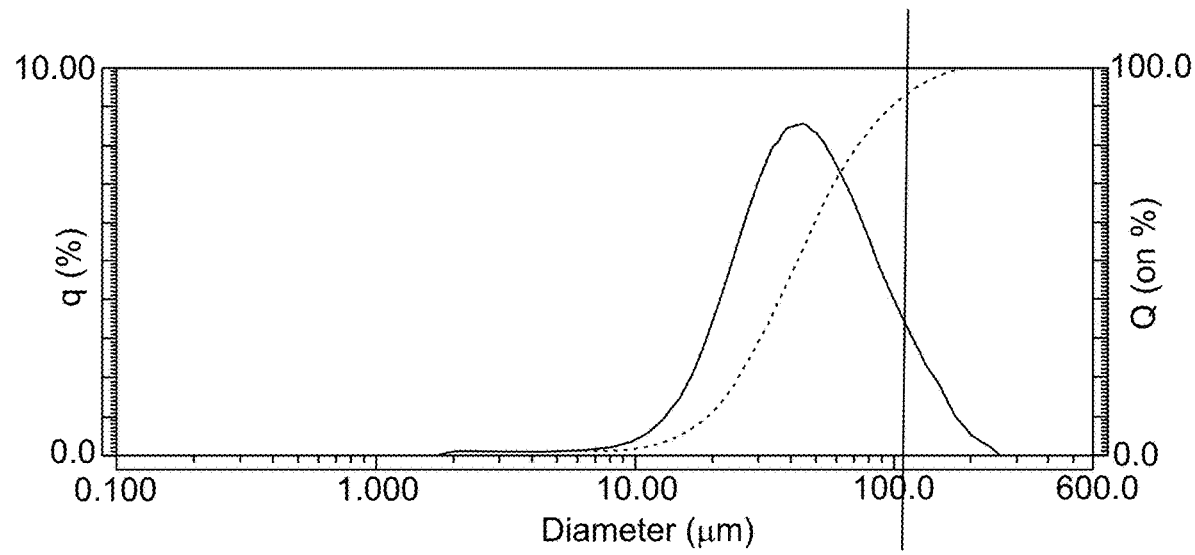

Size Distribution:

The size distribution of the microcapsules obtained in Examples 1-5 was measured and the obtained data is presented in FIG. 1 for Example 1, FIG. 2 for Example 2, FIG. 3 for Example 3 and FIG. 4 for Example 5.

Table 16 below presents the complete size distribution recorded for the microcapsules of Example 1, and presented in FIG. 1.

TABLE 16

| No. | Diameter(μm) | q (%) | Upper % |
|---|---|---|---|
| 1 | 0.115 | 0.000 | 0.000 |
| 2 | 0.131 | 0.000 | 0.000 |
| 3 | 0.150 | 0.000 | 0.000 |
| 4 | 0.172 | 0.000 | 0.000 |
| 5 | 0.197 | 0.000 | 0.000 |
| 6 | 0.226 | 0.000 | 0.000 |
| 7 | 0.259 | 0.000 | 0.000 |
| 8 | 0.296 | 0.000 | 0.000 |
| 9 | 0.339 | 0.000 | 0.000 |
| 10 | 0.389 | 0.000 | 0.000 |
| 11 | 0.445 | 0.000 | 0.000 |
| 12 | 0.510 | 0.000 | 0.000 |
| 13 | 0.584 | 0.000 | 0.000 |
| 14 | 0.669 | 0.000 | 0.000 |
| 15 | 0.766 | 0.000 | 0.000 |
| 16 | 0.877 | 0.000 | 0.000 |
| 17 | 1.005 | 0.000 | 0.000 |
| 18 | 1.151 | 0.000 | 0.000 |
| 19 | 1.318 | 0.000 | 0.000 |
| 20 | 1.510 | 0.000 | 0.000 |
| 21 | 1.729 | 0.000 | 0.000 |
| 22 | 1.981 | 0.000 | 0.000 |
| 23 | 2.269 | 0.000 | 0.000 |
| 24 | 2.599 | 0.000 | 0.000 |
| 25 | 2.976 | 0.000 | 0.000 |
| 26 | 3.409 | 0.000 | 0.000 |
| 27 | 3.905 | 0.000 | 0.000 |
| 28 | 4.472 | 0.000 | 0.000 |
| 29 | 5.122 | 0.000 | 0.000 |
| 30 | 5.867 | 0.000 | 0.000 |
| 31 | 6.720 | 0.000 | 0.000 |
| 32 | 7.697 | 0.000 | 0.000 |
| 33 | 8.816 | 0.000 | 0.000 |
| 34 | 10.097 | 0.000 | 0.000 |
| 35 | 11.565 | 0.000 | 0.000 |
| 36 | 13.246 | 0.109 | 0.109 |
| 37 | 15.172 | 0.148 | 0.257 |
| 38 | 17.377 | 0.204 | 0.460 |
| 39 | 19.904 | 0.282 | 0.742 |
| 40 | 22.797 | 0.389 | 1.131 |
| 41 | 26.111 | 0.529 | 1.660 |
| 42 | 29.907 | 0.708 | 2.368 |
| 43 | 34.255 | 0.930 | 3.298 |
| 44 | 39.234 | 1.201 | 4.500 |
| 45 | 44.938 | 1.526 | 6.025 |
| 46 | 51.471 | 1.913 | 7.939 |
| 47 | 58.953 | 2.378 | 10.317 |
| 48 | 67.523 | 2.940 | 13.257 |
| 49 | 77.339 | 3.618 | 16.875 |
| 50 | 88.583 | 4.429 | 21.304 |
| 51 | 101.460 | 5.372 | 26.676 |
| 52 | 116.210 | 6.412 | 33.088 |
| 53 | 133.103 | 7.459 | 40.547 |
| 54 | 152.453 | 8.353 | 48.900 |
| 55 | 174.616 | 8.893 | 57.792 |
| 56 | 200.000 | 8.901 | 66.694 |
| 57 | 229.075 | 8.306 | 75.000 |
| 58 | 262.376 | 7.201 | 82.200 |
| 59 | 300.518 | 5.808 | 88.008 |
| 60 | 344.206 | 4.388 | 92.396 |
| 61 | 394.244 | 3.144 | 95.539 |
| 62 | 451.556 | 2.168 | 97.707 |
| 63 | 517.200 | 1.427 | 99.135 |
| 64 | 592.387 | 0.865 | 100.000 |

As shown in FIG. 1 and Table 16, the diameter of the microcapsules obtains as described in Example 1 is in the range of from about 3 microns to about 600 microns, with the mean diameter being about 175 microns, the D50 of the microcapsules being about 155 microns, and the D90 of the microcapsules being about 320 microns.

Table 17 below presents the complete size distribution recorded for the microcapsules of Example 2, and presented in FIG. 2.

TABLE 17

| No. | Diameter(μm) | q (%) | Upper % |
|---|---|---|---|
| 1 | 0.115 | 0.000 | 0.000 |
| 2 | 0.131 | 0.000 | 0.000 |
| 3 | 0.150 | 0.000 | 0.000 |
| 4 | 0.172 | 0.000 | 0.000 |
| 5 | 0.197 | 0.000 | 0.000 |
| 6 | 0.226 | 0.000 | 0.000 |
| 7 | 0.259 | 0.000 | 0.000 |
| 8 | 0.296 | 0.000 | 0.000 |
| 9 | 0.339 | 0.000 | 0.000 |
| 10 | 0.389 | 0.000 | 0.000 |
| 11 | 0.445 | 0.000 | 0.000 |
| 12 | 0.510 | 0.000 | 0.000 |
| 13 | 0.534 | 0.000 | 0.000 |
| 14 | 0.669 | 0.000 | 0.000 |
| 15 | 0.766 | 0.000 | 0.000 |
| 16 | 0.877 | 0.000 | 0.000 |
| 17 | 1.005 | 0.000 | 0.000 |
| 18 | 1.151 | 0.000 | 0.000 |
| 19 | 1.318 | 0.000 | 0.000 |
| 20 | 1.510 | 0.129 | 0.129 |
| 21 | 1.729 | 0.166 | 0.295 |
| 22 | 1.981 | 0.195 | 0.490 |
| 23 | 2.269 | 0.200 | 0.690 |
| 24 | 2.599 | 0.196 | 0.886 |
| 25 | 2.976 | 0.173 | 1.059 |
| 26 | 3.409 | 0.150 | 1.209 |
| 27 | 3.905 | 0.123 | 1.332 |
| 28 | 4.472 | 0.000 | 1.332 |
| 29 | 5.122 | 0.000 | 1.332 |
| 30 | 5.867 | 0.000 | 1.332 |
| 31 | 6.720 | 0.000 | 1.332 |
| 32 | 7.697 | 0.000 | 1.332 |
| 33 | 8.816 | 0.000 | 1.332 |
| 34 | 10.097 | 0.000 | 1.332 |
| 35 | 11.565 | 0.000 | 1.332 |
| 36 | 13.246 | 0.000 | 1.332 |
| 37 | 15.172 | 0.138 | 1.470 |
| 38 | 17.377 | 0.203 | 1.673 |
| 39 | 19.904 | 0.311 | 1.984 |
| 40 | 22.797 | 0.489 | 2.474 |
| 41 | 26.111 | 0.774 | 3.248 |
| 42 | 29.907 | 1.213 | 4.461 |
| 43 | 34.255 | 1.845 | 6.306 |
| 44 | 39.234 | 2.689 | 8.995 |
| 45 | 44.938 | 3.713 | 12.708 |
| 46 | 51.471 | 4.823 | 17.531 |
| 47 | 58.953 | 5.883 | 23.419 |
| 48 | 67.523 | 6.779 | 30.198 |
| 49 | 77.339 | 7.399 | 37.597 |
| 50 | 88.583 | 7.710 | 45.307 |
| 51 | 101.460 | 7.732 | 53.039 |
| 52 | 116.210 | 7.506 | 60.545 |
| 53 | 133.103 | 7.081 | 67.626 |
| 54 | 152.453 | 6.499 | 74.125 |
| 55 | 174.616 | 5.797 | 79.923 |
| 56 | 200.000 | 5.019 | 84.942 |
| 57 | 229.075 | 4.204 | 89.145 |
| 58 | 262.376 | 3.402 | 92.548 |
| 59 | 300.518 | 2.660 | 95.208 |
| 60 | 344.206 | 2.016 | 97.224 |
| 61 | 394.244 | 1.489 | 98.713 |
| 62 | 451.556 | 0.827 | 99.540 |
| 63 | 517.200 | 0.460 | 100.000 |
| 64 | 592.387 | 0.000 | 100.000 |

As shown in FIG. 2 and Table 17, the diameter of the microcapsules obtains as described in Example 3 is in the range of from about 3 microns to about 500 microns, with the mean diameter being about 120 microns, the D50 of the microcapsules being about 96 microns, and the D90 of the microcapsules being about 237 microns.

Table 18 below presents the complete size distribution recorded for the microcapsules of Example 3, and presented in FIG. 3.

TABLE 18

| No. | Diameter(μm) | q (%) | Upper % |
|---|---|---|---|
| 1 | 0.115 | 0.000 | 0.000 |
| 2 | 0.131 | 0.000 | 0.000 |
| 3 | 0.150 | 0.000 | 0.000 |
| 4 | 0.172 | 0.000 | 0.000 |
| 5 | 0.197 | 0.000 | 0.000 |
| 6 | 0.226 | 0.000 | 0.000 |
| 7 | 0.259 | 0.000 | 0.000 |
| 8 | 0.296 | 0.000 | 0.000 |
| 9 | 0.339 | 0.000 | 0.000 |
| 10 | 0.389 | 0.000 | 0.000 |
| 11 | 0.445 | 0.000 | 0.000 |
| 12 | 0.510 | 0.000 | 0.000 |
| 13 | 0.584 | 0.000 | 0.000 |
| 14 | 0.669 | 0.000 | 0.000 |
| 15 | 0.766 | 0.000 | 0.000 |
| 16 | 0.877 | 0.000 | 0.000 |
| 17 | 1.005 | 0.000 | 0.000 |
| 18 | 1.151 | 0.000 | 0.000 |
| 19 | 1.318 | 0.000 | 0.000 |
| 20 | 1.510 | 0.000 | 0.000 |
| 21 | 1.729 | 0.112 | 0.112 |
| 22 | 1.981 | 0.137 | 0.250 |
| 23 | 2.269 | 0.147 | 0.397 |
| 24 | 2.599 | 0.151 | 0.547 |
| 25 | 2.976 | 0.140 | 0.687 |
| 26 | 3.409 | 0.127 | 0.814 |
| 27 | 3.905 | 0.107 | 0.920 |
| 28 | 4.472 | 0.000 | 0.920 |
| 29 | 5.122 | 0.000 | 0.920 |
| 30 | 5.867 | 0.000 | 0.920 |
| 31 | 6.720 | 0.000 | 0.920 |
| 32 | 7.697 | 0.000 | 0.920 |
| 33 | 8.816 | 0.000 | 0.920 |
| 34 | 10.097 | 0.000 | 0.920 |
| 35 | 11.565 | 0.000 | 0.920 |
| 36 | 13.246 | 0.000 | 0.920 |
| 37 | 15.172 | 0.000 | 0.920 |
| 38 | 17.377 | 0.000 | 0.920 |
| 39 | 19.904 | 0.000 | 0.920 |
| 40 | 22.797 | 0.000 | 0.920 |
| 41 | 26.111 | 0.143 | 1.064 |
| 42 | 29.907 | 0.233 | 1.297 |
| 43 | 34.255 | 0.397 | 1.694 |
| 44 | 39.234 | 0.700 | 2.394 |
| 45 | 44.936 | 1.244 | 3.636 |
| 46 | 51.471 | 2.174 | 5.812 |
| 47 | 58.953 | 3.643 | 9.455 |
| 48 | 67.523 | 5.705 | 15.161 |
| 49 | 77.339 | 8.170 | 23.330 |
| 50 | 88.583 | 10.519 | 33.850 |
| 51 | 101.460 | 12.068 | 45.918 |
| 52 | 116.210 | 12.311 | 58.229 |
| 53 | 133.103 | 11.237 | 69.466 |
| 54 | 152.453 | 9.292 | 78.759 |
| 55 | 174.616 | 7.089 | 85.847 |
| 56 | 200.000 | 5.101 | 90.949 |
| 57 | 229.075 | 3.539 | 94.488 |
| 58 | 262.376 | 2.420 | 96.908 |
| 59 | 300.518 | 1.659 | 98.566 |
| 60 | 344.206 | 0.922 | 99.488 |
| 61 | 394.2.44 | 0.512 | 100.000 |
| 62 | 451.556 | 0.000 | 100.000 |
| 63 | 517.200 | 0.000 | 100.000 |
| 64 | 592.387 | 0.000 | 100.000 |

As shown in FIG. 3 and Table 18, the diameter of the microcapsules obtains as described in Example 3 is in the range of from about 3 microns to about 400 microns, with the mean diameter being about 120 microns, the D50 of the microcapsules being about 106 microns, and the D90 of the microcapsules being about 195 microns.

TABLE 19

| No. | Diameter(μm) | q (%) | Upper % |
|---|---|---|---|
| 1 | 0.115 | 0.000 | 0.000 |
| 2 | 0.131 | 0.000 | 0.000 |
| 3 | 0.150 | 0.000 | 0.000 |
| 4 | 0.172 | 0.000 | 0.000 |
| 5 | 0.197 | 0.000 | 0.000 |
| 6 | 0.226 | 0.000 | 0.000 |
| 7 | 0.259 | 0.000 | 0.000 |
| 8 | 0.296 | 0.000 | 0.000 |
| 9 | 0.339 | 0.000 | 0.000 |
| 10 | 0.389 | 0.000 | 0.000 |
| 11 | 0.445 | 0.000 | 0.000 |
| 12 | 0.510 | 0.000 | 0.000 |
| 13 | 0.584 | 0.000 | 0.000 |
| 14 | 0.669 | 0.000 | 0.000 |
| 15 | 0.766 | 0.000 | 0.000 |
| 16 | 0.877 | 0.000 | 0.000 |
| 17 | 1.005 | 0.000 | 0.000 |
| 18 | 1.151 | 0.000 | 0.000 |
| 19 | 1.318 | 0.000 | 0.000 |
| 20 | 1.510 | 0.000 | 0.000 |
| 21 | 1.729 | 0.000 | 0.000 |
| 22 | 1.981 | 0.107 | 0.107 |
| 23 | 2.269 | 0.110 | 0.218 |
| 24 | 2.599 | 0.111 | 0.329 |
| 25 | 2.976 | 0.109 | 0.437 |
| 26 | 3.409 | 0.105 | 0.542 |
| 27 | 3.905 | 0.104 | 0.646 |
| 28 | 4.472 | 0.106 | 0.752 |
| 29 | 5.122 | 0.115 | 0.867 |
| 30 | 5.867 | 0.133 | 0.999 |
| 31 | 6.720 | 0.151 | 1.151 |
| 32 | 7.697 | 0.200 | 1.351 |
| 33 | 8.816 | 0.282 | 1.633 |
| 34 | 10.097 | 0.420 | 2.054 |
| 35 | 11.565 | 0.547 | 2.700 |
| 36 | 13.246 | 1.007 | 3.707 |
| 37 | 15.172 | 1.553 | 5.260 |
| 38 | 17.377 | 2.329 | 7.589 |
| 39 | 19.904 | 3.344 | 10.934 |
| 40 | 22.797 | 4.542 | 15.476 |
| 41 | 26.111 | 5.808 | 21.284 |
| 42 | 29.907 | 6.978 | 28.262 |
| 43 | 34.255 | 7.892 | 36.154 |
| 44 | 39.234 | 8.434 | 44.588 |
| 45 | 44.938 | 8.557 | 53.145 |
| 46 | 51.471 | 8.279 | 61.424 |
| 47 | 58.953 | 7.675 | 69.099 |
| 48 | 67.523 | 6.855 | 75.954 |
| 49 | 77.339 | 5.911 | 81.865 |
| 50 | 88.583 | 4.930 | 86.795 |
| 51 | 101.460 | 3.987 | 90.782 |
| 52 | 116.210 | 3.134 | 93.916 |
| 53 | 133.103 | 2.404 | 96.319 |
| 54 | 152.453 | 1.808 | 98.127 |
| 55 | 174.616 | 1.005 | 99.132 |
| 56 | 200.000 | 0.558 | 99.690 |
| 57 | 229.075 | 0.310 | 100.000 |
| 58 | 262.376 | 0.000 | 100.000 |
| 59 | 300.518 | 0.000 | 100.000 |
| 60 | 344.206 | 0.000 | 100.000 |
| 61 | 394.244 | 0.000 | 100.000 |
| 62 | 451.556 | 0.000 | 100.000 |
| 63 | 517.200 | 0.000 | 100.000 |
| 64 | 592.387 | 0.000 | 100.000 |

As shown in FIG. 4 and Table 19, the diameter of the microcapsules obtains as described in Example 5 is in the range of from about 3 microns to about 250 microns, with the mean diameter being about 120 microns, the D50 of the microcapsules being about 96 microns, and the D90 of the microcapsules being about 237 microns.

Loose Bulk Density:

The loose bulk density of the microcapsules obtained in Example 1 was determined as ranging from about 300 to about 450 grams/liter (from about 0.30 to about 0.45 gram/cm$^3$), or from about 300 to about 380 grams/liter (from about 0.30 to about 0.38 gram/cm$^3$) or from about 300 to about 340 grams/liter (from about 0.30 to about 0.4 gram/cm$^3$).

The loose bulk density of the microcapsules obtained in Example 2 was determined as ranging from about 360 to about 460 grams/liter (from about 0.36 to about 0.46 gram/cm$^3$), or from about 380 to 440 grams/liter (from about 0.38 to about 0.44 gram/cm$^3$), or from about 400 to 420 grams/liter (from about 0.40 to about 0.42 gram/cm$^3$).

The loose bulk density of the microcapsules obtained in Example 3 was determined as ranging from about 140 to about 360 grams/liter (from about 0.14 to about 0.36 gram/cm$^3$), or from about 200 to 300 grams/liter (from about 0.20 to about 0.30 gram/cm$^3$), or from about 240 to about 260 grams/liter (from about 0.24 to about 0.26 gram/cm$^3$).

The loose bulk density of the microcapsules obtained in Example 5 was determined as ranging from about 420 to about 560 grams/liter (from about 0.42 to about 0.56 gram/cm$^3$), or from about 450 to about 530 grams/liter (from about 0.45 to about 0.53 gram/cm$^3$), or from about 480 to about 500 grams/liter (from about 0.48 to about 0.50 gram/cm$^3$).

Masking:

Quantitative measurements of the masking effect provided by encapsulating bismuth oxychloride, the X-Rite measurement technique using the CIE Color Systems (based on the CIE L*a*b* color scale, wherein L* defines lightness, a* denotes the red/green value and b* the yellow/blue value) was used. The standard illuminant applied for these measurements was daylight.

Quantitative values were obtained by integrating values/data measured for three visual elements of color: hue (namely, how we perceive an object's color), chroma (the vividness or dullness of a color namely, how close the color is to either gray or the pure hue), and degree of lightness (namely classifying whether a color is light or dark).

Table 20 below presents the shift in lightness on the lightness scale L* of the present microcapsules relative to the bismuth oxychloride-containing raw material Timiron® Liquid Silver (DL*). The positive DL* values presented in Table 16 denote a shift on the lightness scale in the direction of substantially lighter, brighter color for the microcapsules of the invention compared to the raw material, which is indicative of the masking effect.

TABLE 20

| Example No. | DL* relative to Timiron ® Liquid Silver Raw material |
|---|---|
| 1 | 8.45 |
| 2 | 5.71 |
| 3 | 9.96 |
| 5 | 13.47 |

Light Reflectance:

Light reflectance is measured using polarized goniophotometer system with a halogen lamp. Both input and detected light are polarized. The incident light angle is 45° and a convergent angle ranges over 20-75°, with a moving detector. The detection polarizer can be rotated to collect either parallel or perpendicular polarized light. Each quantity of light can be calculated from the quantity of parallel filtered and vertically filtered light. The quantity of internally reflected light:

$$I \text{internally reflected light} = 2 \times I \text{vertical}$$

The quantity of surface-reflected light:

$I\text{surface-reflected light} = I\text{parallel} - I\text{vertical}$

The quantity of totally reflected light:

$I\text{total} = I\text{internally} + I\text{surface} = I\text{parallel} + I\text{vertical}$ Icrossed: the quantity of light passing through the crossed polarized filters.
Iparallel: the quantity of light passing through the parallel polarized filters.

Example 7

Stability

In order to assess the stability of the microcapsules, various formulations were prepared, and microcapsules (3% of total formulation weight) were added thereto.
The following formulations were tested:
(i) a gel formulation prepared by mixing carbomer with water (1-1.5% carbomer by weight);
(ii) a water-in-oil emulsion, pH of about 7, comprising the following ingredients, and prepared by mixing Phase A and Phase B for 15 minutes at 6,000 rpm at a temperature of 70-75° C., and adding Phase C at 40° C., in accordance with the following table:

| Trade name | INCI name | % | Functions | 1000 grams |
|---|---|---|---|---|
| Phase A - Oil | | | | |
| Tegin | Glyceryl Stearate SE | 8 | Emulsifier | 80 g |
| Stearic acid | Stearic acid | 2 | Emulsifier | 20 g |
| Captex 8000 | Tricaprilin | 12 | Emollient | 120 g |
| Saboderm AB | C12-15 Alkyl Benzoate | 12 | Emollient | 120 g |
| Phase B - Water | | | | |
| Deionized Water | Deionized Water | 60.5 | Solvent | 605 g |
| Propylene Glycol | Propylene Glycol | 5 | Humectant | 50 g |
| Phase C - Preservatives | | | | |
| Glydant | DMDM Hydantoin | 0.5 | Preservative | 5 g |

(iii) a water-in-oil emulsion, comprising the following ingredients, and prepared by separately mixing the ingredients of Phase A and Phase B until uniform mixtures are obtained; adding Phase B to Phase A while mixing with a paddle mixer and then, in small increments, adding Phase C, while increasing, slowly, the mixing speed as the product begins to thicken; and thereafter adding phase D and homogenizing the obtained emulsion for about 3 minutes, in accordance with the following table:

| Phase | Ingredient | INCI Name | % | Manufacturer |
|---|---|---|---|---|
| Phase A | Dow Corning ES-5600 Silicone Glycerol Emulsifier | Cetyl Diglyceryl Tris (Trimethylsiloxy) silylethyl Dimethicone | 4.2 | Dow Corning |
| | Dermofeel Sensolv | Isoamyl Laurate | 1.9 | Dr. Straetmans |
| | Dermosoft MCT | Tricaprylin | 3.2 | Dr. Straetmans |
| | Almond Oil | *Prunus Amygdalus Dulcis* (Sweet Almond) Oil | 0.9 | Interaxion |
| | Cetiol OE | Dicaprylyl Ether | 2.2 | Cognis |
| | Euxyl PE 9010 | Phenoxyethanol Ethylhexylglycerin | 1.0 | Schülke & Mayr GmbH |
| Phase B | Dow Corning ES-5600 Silicone Glycerol Emulsifier | Cetyl Diglyceryl Tris (Trimethylsiloxy) silylethyl Dimethicone | 1.8 | Dow Corning |
| | Dow Corning 556 Cosmetic grade fluid | Phenyl Trimethicone | 5.37 | Dow Corning |
| | UV Cut TiO2-60-VL | Titanium Dioxide & Coconut Alkanes & Polyhydroxystearic Acid & Stearic Acid & Alumina & Coco-Caprylate/Caprate | 5.0 | GRANT |
| | Gransil DMG-6 | Dimethicone & Polysilicone-11 | 4.0 | GRANT |
| Phase C | Water | | 59.01 | |
| | Dead Sea Salt | | 1.0 | |
| | Glycerin | | 3.75 | Cremer |
| Phase D | Perfume COCO M | Parfum (Fragrance) | 0.3 | Torpaz |
| | Gransil PSQ | Polymethylsilsesquioxane | 1.9 | GRANT |

The microcapsules of Examples 1-5 hereinabove were added gradually to each formulation at 40° C., and the mixture was subjected for at least 3 hours to low shear mixing at up to 100 rpm. The color of the formulation was monitored during incubation, and samples of the formulation were taken and observed under light microscope. It was found that at least 90% of microcapsules maintained their shape and no leaking of bismuth oxychloride from the microcapsules to the formulation was observed, for each of the tested formulations.

Example 8

Rupturability

Figure 5A:
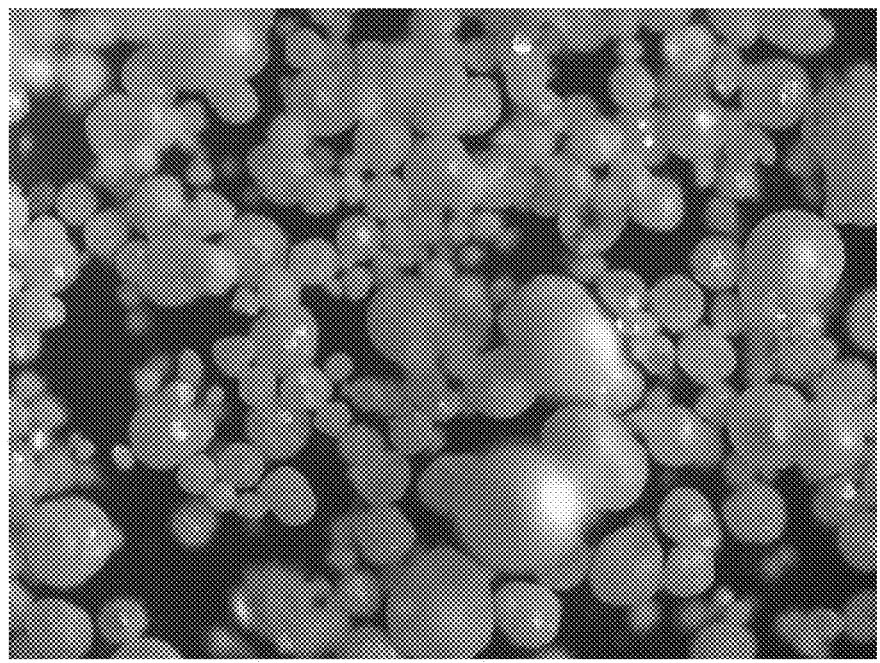
FIGS. 5A-C present images of a plurality of microcapsules obtained as described in Example 1, before subjecting the microcapsules to shear forces (FIG. 5A) and after application of rubbing by 2 circle motions (FIG. 5B) and by 4 circle motions (FIG. 5C).
Figure 5B:
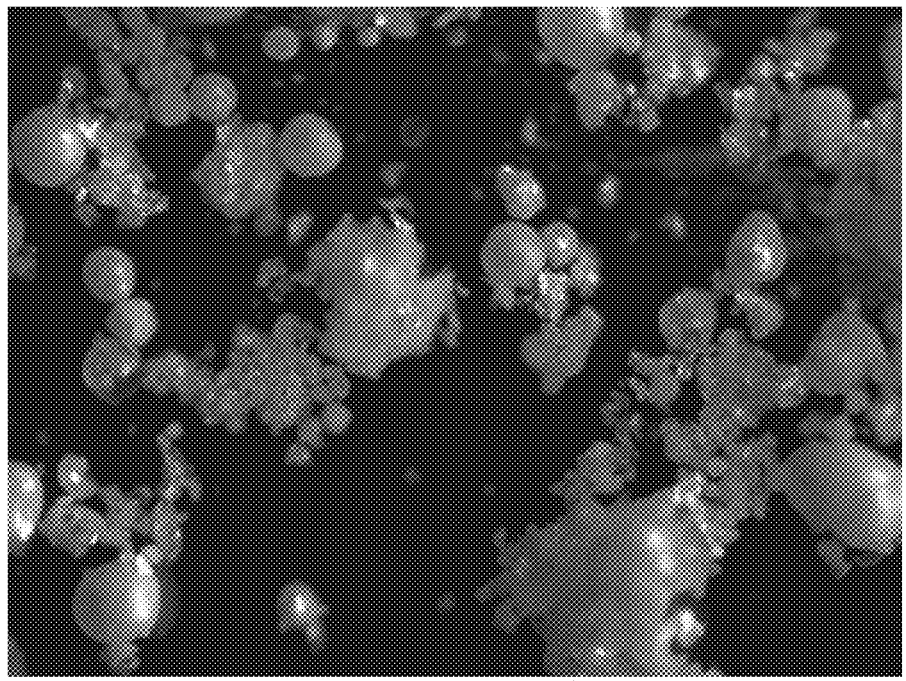
Figure 5C:
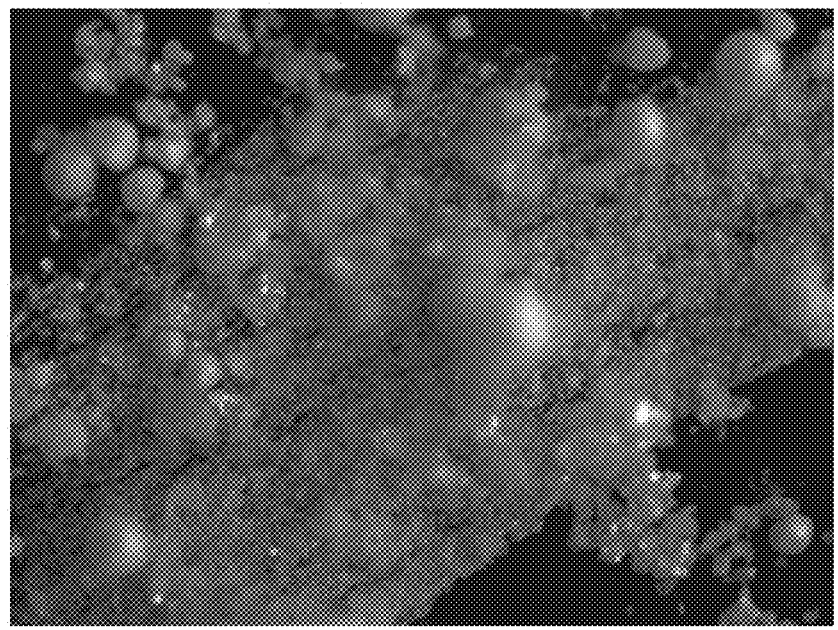

The rupturability of the microcapsules upon application of shear forces was tested by imaging the microcapsules before and after subjecting the microcapsules to rubbing, by application of circle motions FIGS. 5A-C present images, taken using Zeiss light microscope with imaging software ZEN 2.1 from Zeiss, of microcapsules as described in Example 1 hereinabove, before (FIG. 5A) application of shear forces, and after subjecting the microcapsules to rubbing by 2 circle motions (FIG. 5B) and 4 circle motions (FIG. 5C). As shown therein, upon rubbing, the microcapsules rupture and consequently release the encapsulated reflective agent into the surrounding.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A microcapsule comprising an inner core enveloped by an outer shell formed of a wall-forming polymeric material, said inner core comprising particles of bismuth oxychloride dispersed in 2-ethylhexyl hydroxystearate, and said outer shell further comprises an opaque substance and a fatty acid salt,
  wherein an amount of said inner core ranges from about 70% to about 90%, by weight, of the total weight of the microcapsule,
  and wherein:
  said wall-forming polymeric material is selected from selected from the group consisting of poly(methyl methacrylate), poly(methyl methacrylate)-co-(methacrylic acid), cellulose acetate, and an acrylate/ammonium methacrylate copolymer;
  an amount of said wall-forming polymeric material ranges from about 5% to about 15%, by weight, of the total weight of the microcapsule;
  said opaque substance is titanium dioxide;
  an amount of said opaque substance ranges from about 10 to about 40%, by weight, of the total weight of the microcapsule;
  said fatty acid salt is magnesium stearate; and
  an amount of said fatty acid salt ranges from about 1 to about 2%, by weight, of the total weight of the microcapsule.

2. The microcapsule of claim 1, further comprising a plasticizer.

3. The microcapsule of claim 1, being a single-layer microcapsule.

4. A plurality of microcapsules, at least a portion of said microcapsules comprising the microcapsules of claim 1.

5. The microcapsules of claim 4, wherein a mean size of said plurality of microcapsules ranges from about 100 μm to about 200 μm.

* * * * *